United States Patent
Baruch

(10) Patent No.: US 7,087,025 B2
(45) Date of Patent: Aug. 8, 2006

(54) BLOOD PRESSURE DETERMINATION BASED ON DELAY TIMES BETWEEN POINTS ON A HEARTBEAT PULSE

(75) Inventor: Martin C. Baruch, Charlottesville, VA (US)

(73) Assignee: Empirical Technologies Corporation, Charlottesville, VA (US)

( * ) Notice: Subject to any disclaimer, the term of this patent is extended or adjusted under 35 U.S.C. 154(b) by 0 days.

(21) Appl. No.: 10/502,932

(22) PCT Filed: Jan. 29, 2003

(86) PCT No.: PCT/US03/02490

§ 371 (c)(1),
(2), (4) Date: Jul. 29, 2004

(87) PCT Pub. No.: WO03/063687

PCT Pub. Date: Aug. 7, 2003

(65) Prior Publication Data

US 2005/0096551 A1   May 5, 2005

Related U.S. Application Data

(60) Provisional application No. 60/352,213, filed on Jan. 29, 2002, provisional application No. 60/371,399, filed on Apr. 11, 2002, provisional application No. 60/387,435, filed on Jun. 11, 2002, provisional application No. 60/410,349, filed on Sep. 13, 2002.

(51) Int. Cl.
*A61B 5/00*   (2006.01)

(52) U.S. Cl. .................... 600/500; 600/485

(58) Field of Classification Search ......... 600/485–503
See application file for complete search history.

(56) References Cited

U.S. PATENT DOCUMENTS

| | | | | |
|---|---|---|---|---|
| 4,245,648 | A | * 1/1981 | Trimmer et al. | 600/493 |
| 5,241,964 | A | 9/1993 | McQuilkin | 128/672 |
| 5,450,852 | A | 9/1995 | Archibald et al. | 128/672 |
| 5,505,206 | A | 4/1996 | Walloch | 128/681 |
| 5,533,511 | A | * 7/1996 | Kaspari et al. | 600/485 |
| 5,590,661 | A | 1/1997 | Ohmori et al. | 128/672 |
| 5,623,933 | A | * 4/1997 | Amano et al. | 600/500 |
| 5,640,964 | A | 6/1997 | Archibald et al. | 128/672 |
| 5,642,733 | A | 7/1997 | Archibald et al. | 128/672 |
| 5,649,542 | A | 7/1997 | Archibald et al. | 128/681 |
| 5,720,292 | A | 2/1998 | Poliac | 128/672 |
| 5,722,414 | A | 3/1998 | Archibald et al. | 128/672 |
| 5,738,103 | A | 4/1998 | Poliac | 128/672 |
| 5,797,850 | A | 8/1998 | Archibald et al. | 600/494 |
| 5,832,924 | A | 11/1998 | Archibald et al. | 128/672 |
| 5,873,834 | A | * 2/1999 | Yanagi et al. | 600/485 |
| 5,938,618 | A | 8/1999 | Archibald et al. | 600/485 |
| 5,941,828 | A | 8/1999 | Archibald et al. | 600/494 |
| 5,993,394 | A | 11/1999 | Poliac | 600/485 |
| 6,017,314 | A | 1/2000 | Poliac | 600/485 |

(Continued)

FOREIGN PATENT DOCUMENTS

AU   749372   6/2000

(Continued)

*Primary Examiner*—Robert L. Nasser
(74) *Attorney, Agent, or Firm*—Sheldon H. Parker

(57) ABSTRACT

Blood pressure determination with resolution sufficient to resolve Pulsus Paradoxus is based on measurement of delay time between points on a heartbeat pulse.

10 Claims, 11 Drawing Sheets

U.S. PATENT DOCUMENTS

| | | | |
|---|---|---|---|
| 6,099,477 A | 8/2000 | Archibald et al. | 600/494 |
| 6,106,478 A * | 8/2000 | Tochikubo et al. | 600/494 |
| 6,132,382 A | 10/2000 | Archibald et al. | 600/485 |
| 6,159,157 A | 12/2000 | Archibald et al. | 600/485 |
| 6,241,679 B1 | 6/2001 | Curran | 600/485 |
| 6,245,022 B1 | 6/2001 | Archibald et al. | 600/485 |
| 6,325,761 B1 | 12/2001 | Jay | 600/485 |
| 6,340,349 B1 | 1/2002 | Archibald et al. | 600/494 |
| D458,375 S | 6/2002 | Thede | D24/165 |
| 6,471,646 B1 | 10/2002 | Thede | 600/301 |
| 6,558,335 B1 | 5/2003 | Thede | 600/503 |
| 6,589,185 B1 | 7/2003 | Archibald et al. | 600/494 |
| 2003/0158487 A1 | 8/2003 | Thede et al. | 600/485 |
| 2003/0208127 A1 | 11/2003 | Archibald et al. | 600/494 |
| 2003/0216653 A1 | 11/2003 | Poliac et al. | 600/500 |

FOREIGN PATENT DOCUMENTS

| | | |
|---|---|---|
| WO | WO 92/07508 | 5/1992 |
| WO | WO 95/13014 | 5/1995 |
| WO | WO 96/25087 | 8/1996 |
| WO | WO 96/25091 | 8/1996 |
| WO | WO 96/25092 | 8/1996 |
| WO | WO 98/04188 | 2/1998 |
| WO | WO 98/04192 | 2/1998 |
| WO | WO 99/08591 | 2/1999 |
| WO | WO 00/22983 | 4/2000 |
| WO | WO 00/64333 | 11/2000 |
| WO | WO 00/71021 | 11/2000 |
| WO | WO 02/41756 | 5/2002 |
| WO | WO 03/007816 | 1/2003 |

* cited by examiner

FIG. 1
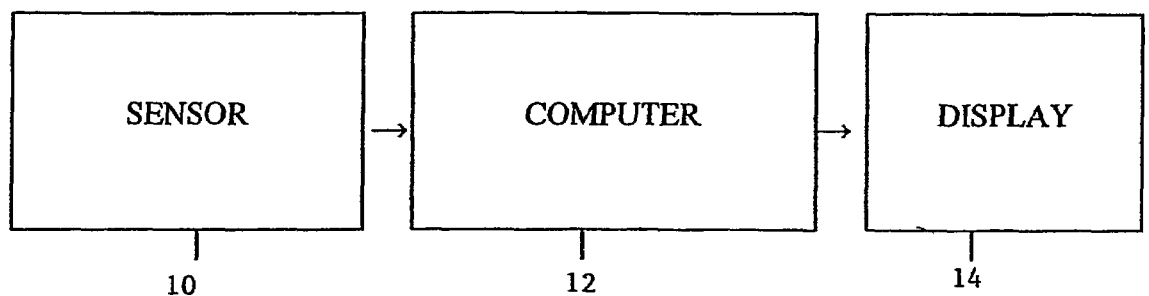
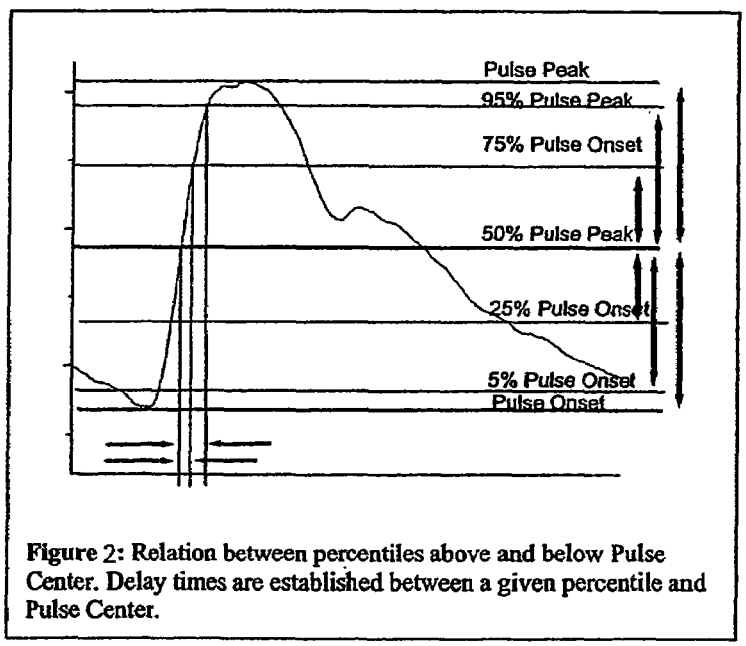
Figure 2: Relation between percentiles above and below Pulse Center. Delay times are established between a given percentile and Pulse Center.

AB
↓

Step 8

An effective delay time is then calculated using the expression $$\Delta T = \frac{\sum_i w_i(\delta t_i - \delta t_1)}{\sum_i w_i}$$

where the $\delta t_i$ are the individual delay times and $\delta t_1$ is the first delay-time, located at around 20% full-amplitude, or close to the onset of the pulse, but above potential noise sources. The $w_i$'s are weighting factors, usually all set equal to one.

↓

Step 9

The conversion from delay time to pressure is accomplished using the expression $$p = \frac{2}{\xi} \ln\left(\frac{\Delta T}{d} \sqrt{\frac{hE_o}{2p\alpha}}\right) + C$$

where E is the Young's modulus, $\alpha$ is the artery's diameter, $p$ is the fluid density, d is the arterial wall thickness, and $\xi$ and C are constants. $\xi$ and C are adjusted to achieve agreement with calibrated pressure reading (obtained by cuff or other means).

FIG. 3B

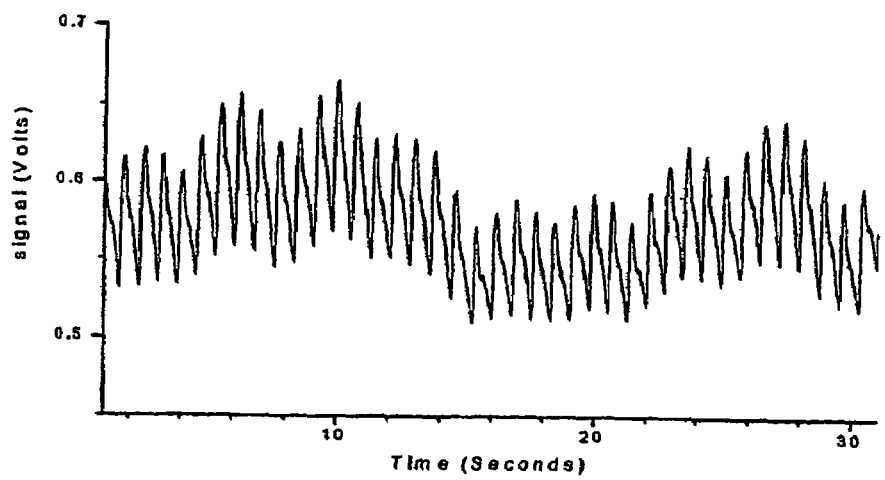
Figure 4: Raw data stream about 30 seconds long. Breathing signal and other signals, such as motion, modulates heartbeat signal. Notice significant DC offset.
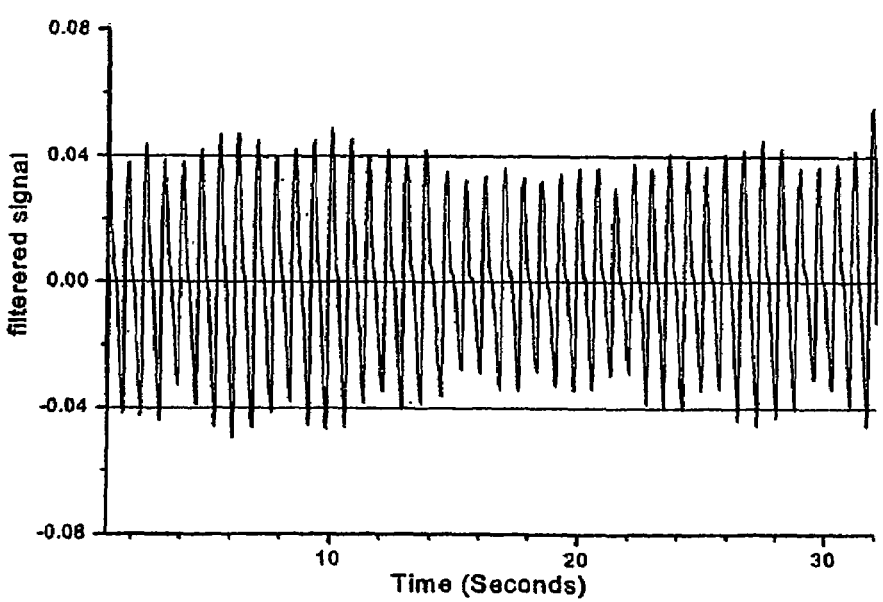
Figure 5: filtered data stream (FFT filter: 0.7Hz to 20 Hz). Heartbeat signal is now centered about zero. Some modulations remain.

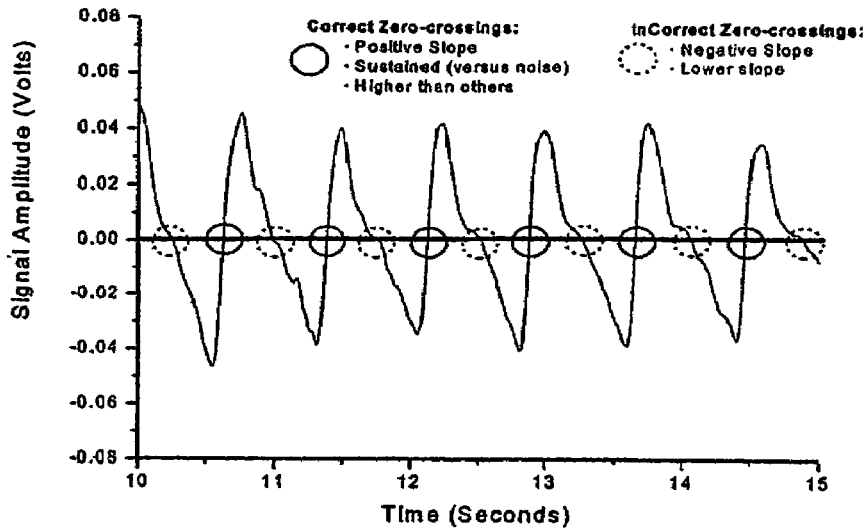
Figure 6: Zero-crossing detection. The crossings of interest are established by determining the slope of the signal at the crossing (sign, amplitude).
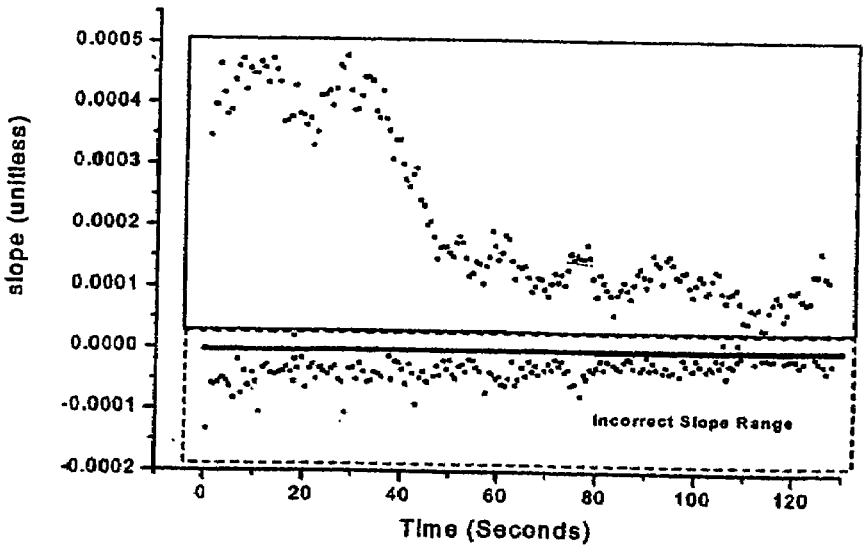
Figure 7: Slope values obtained from 20-point fits about each zero-crossing of a 120 second data run. The onset of each heartbeat pulse features a positive & higher amplitude slope than the tail end of the pulse.

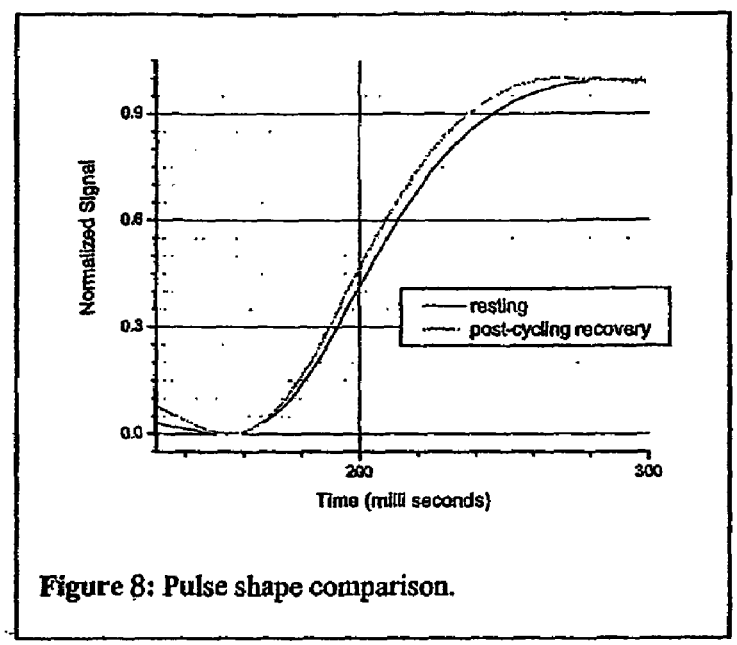
Figure 8: Pulse shape comparison.
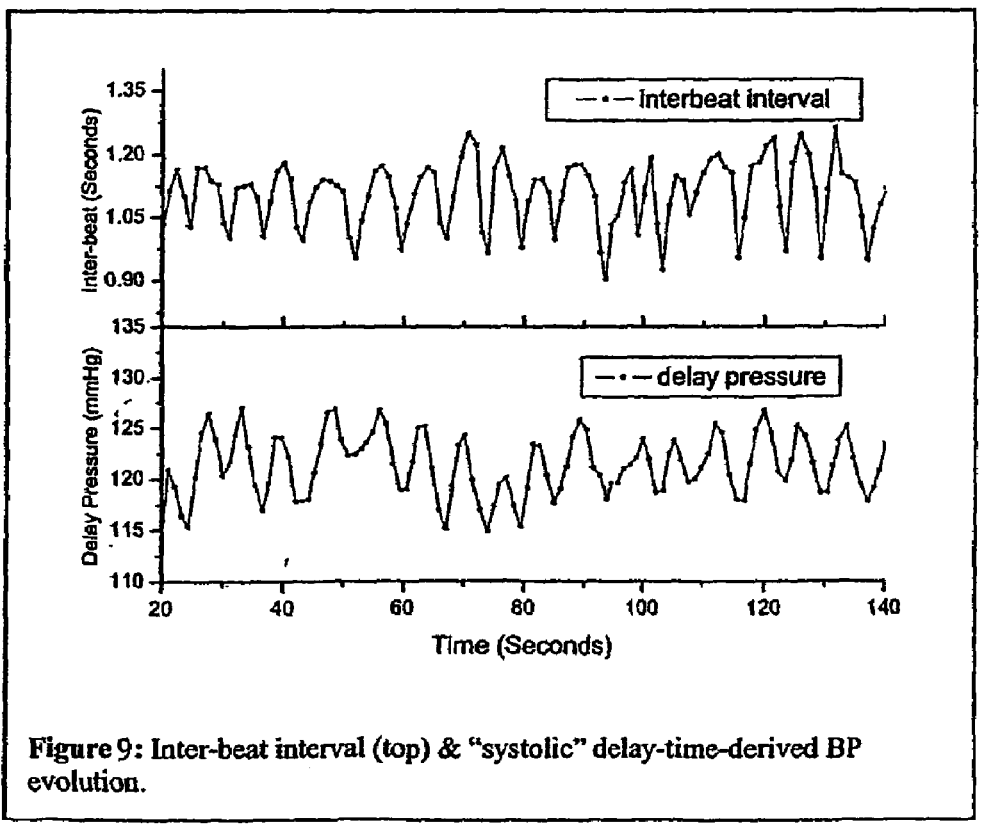
Figure 9: Inter-beat interval (top) & "systolic" delay-time-derived BP evolution.

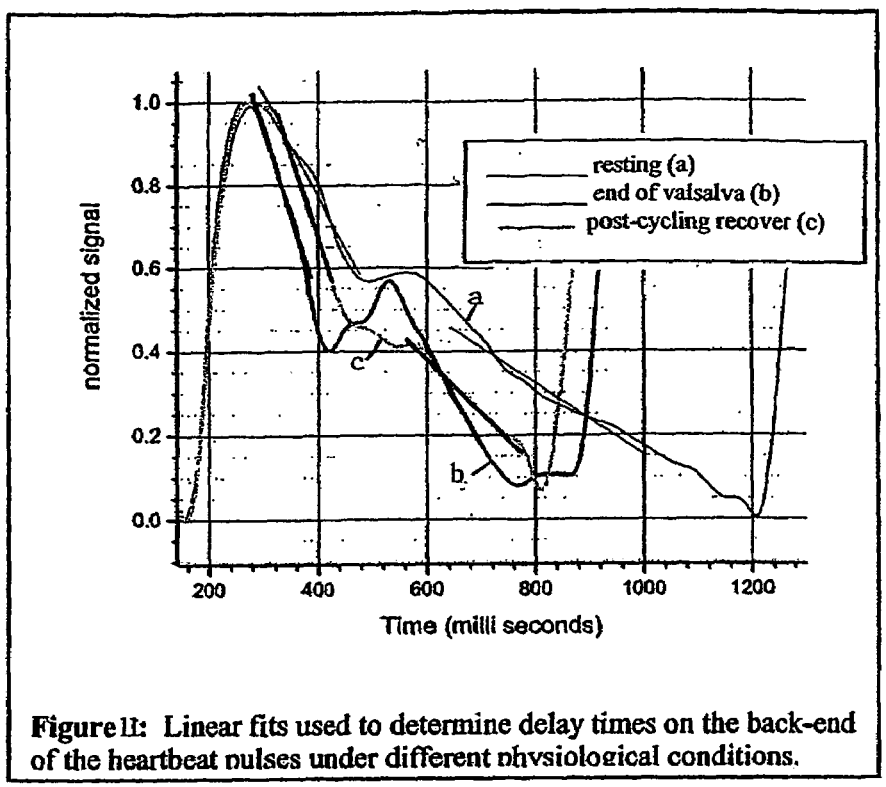
Figure 11: Linear fits used to determine delay times on the back-end of the heartbeat pulses under different physiological conditions.
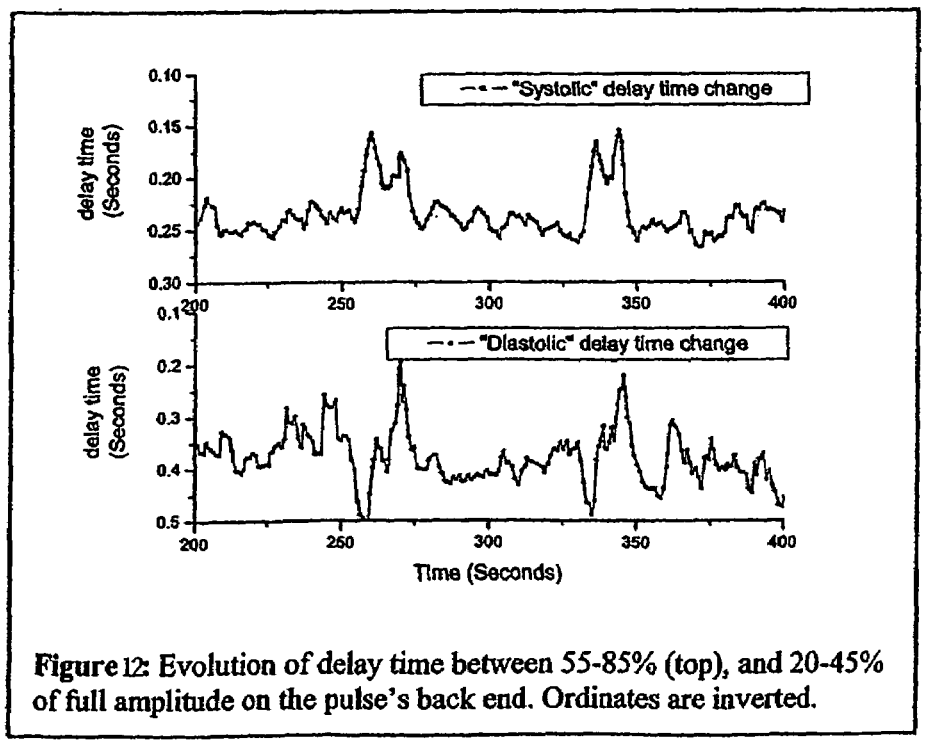
Figure 12: Evolution of delay time between 55-85% (top), and 20-45% of full amplitude on the pulse's back end. Ordinates are inverted.

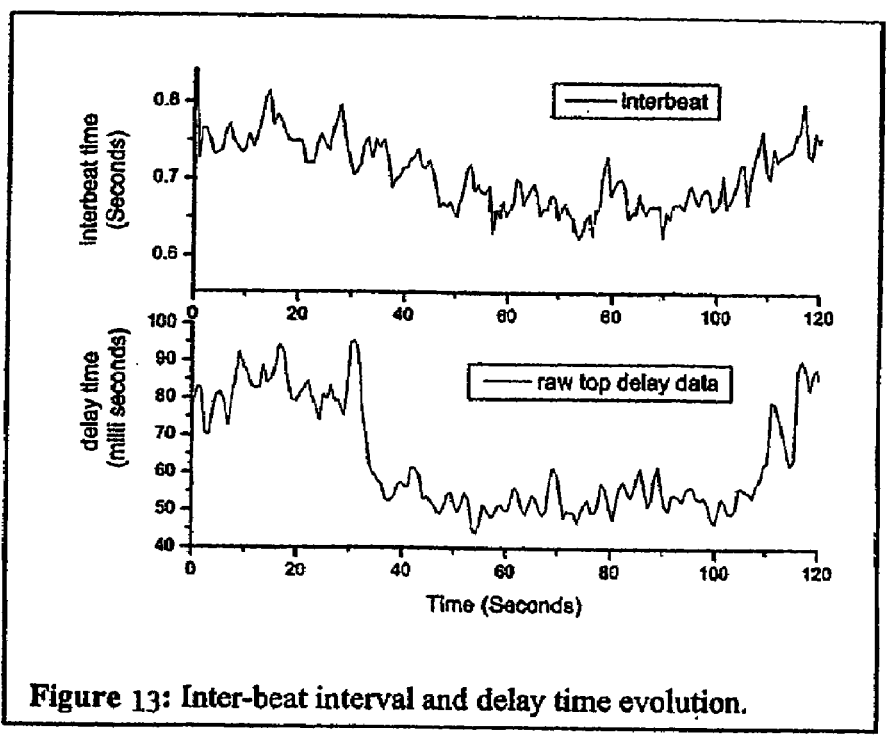
Figure 13: Inter-beat interval and delay time evolution.
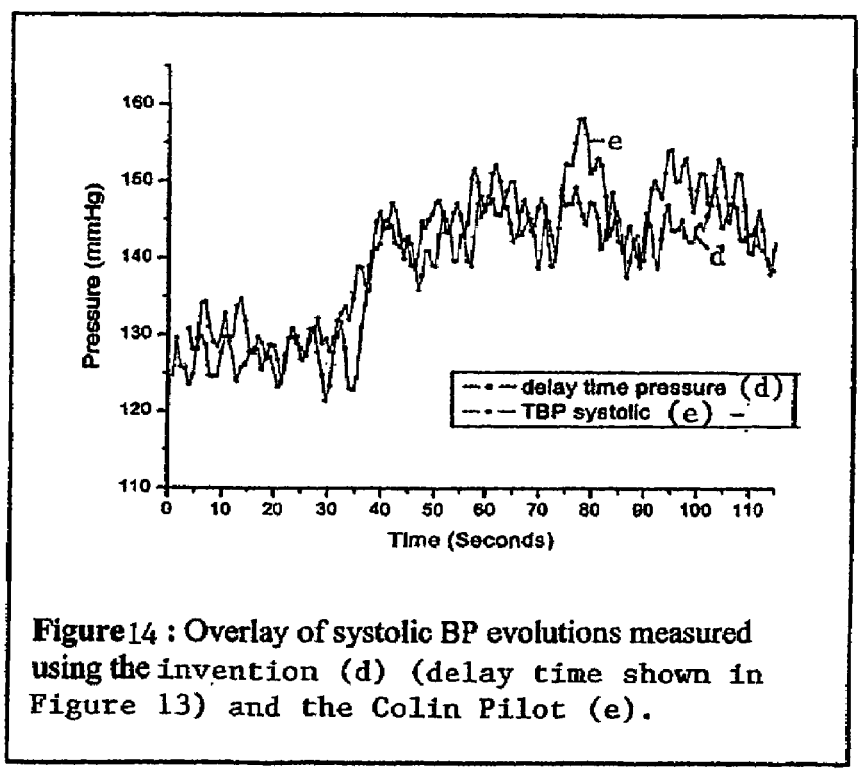
Figure 14: Overlay of systolic BP evolutions measured using the invention (d) (delay time shown in Figure 13) and the Colin Pilot (e).

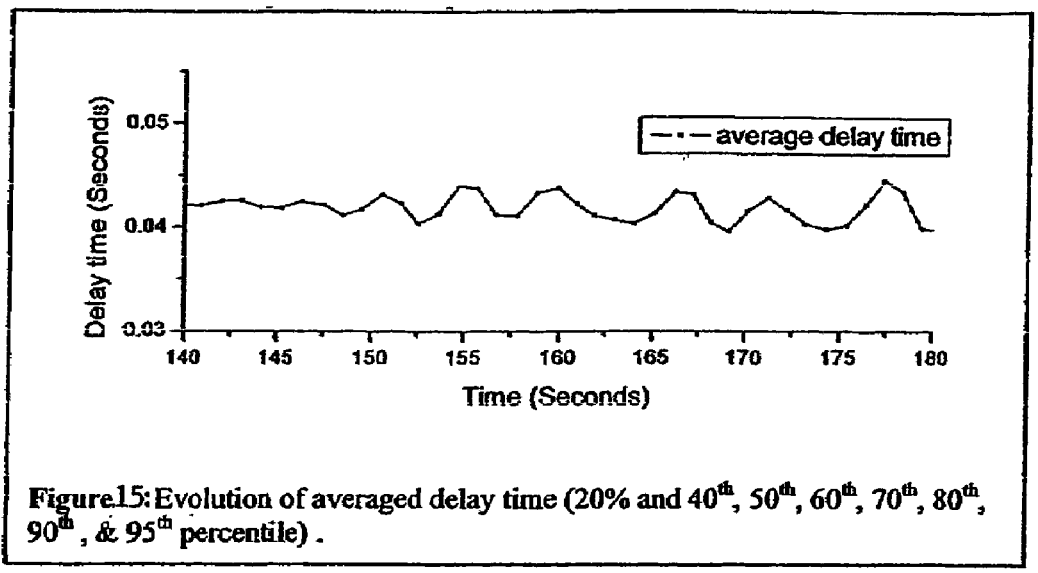
Figure 15: Evolution of averaged delay time (20% and $40^{th}$, $50^{th}$, $60^{th}$, $70^{th}$, $80^{th}$, $90^{th}$, & $95^{th}$ percentile).
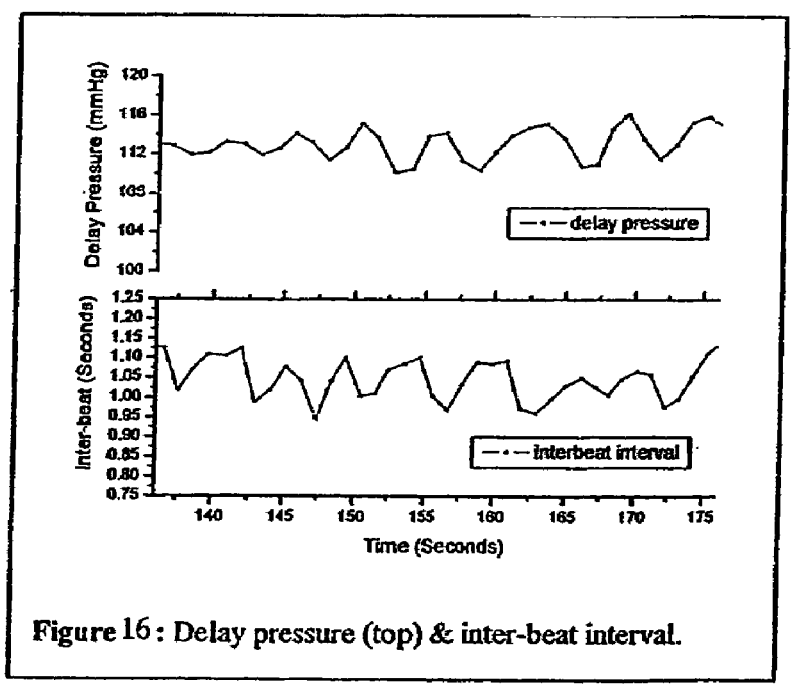
Figure 16: Delay pressure (top) & inter-beat interval.

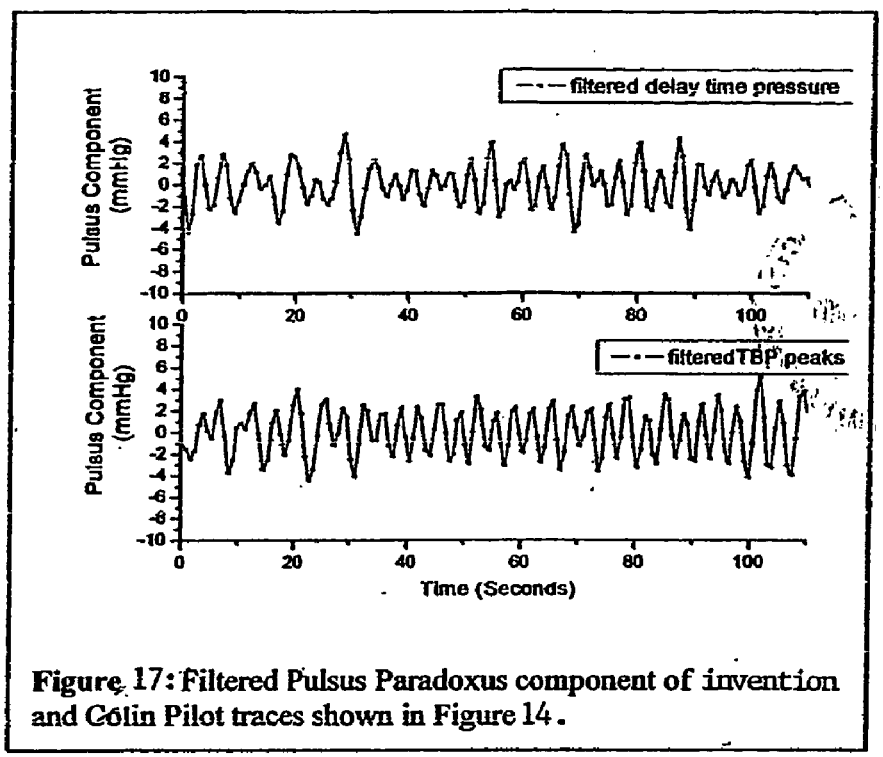
Figure 17: Filtered Pulsus Paradoxus component of invention and Colin Pilot traces shown in Figure 14.

BLOOD PRESSURE DETERMINATION BASED ON DELAY TIMES BETWEEN POINTS ON A HEARTBEAT PULSE

CROSS REFERENCE TO RELATED APPLICATIONS

This application claims the benefit of provisional application 60/352,213 filed Jan. 29, 2002; 60/371,399 filed Apr. 11, 2002; 60/387,435 filed Jun. 11, 2002; and 60/410,349 filed Sep. 13, 2002, all of which are incorporated herein by reference.

BACKGROUND OF THE INVENTION

This invention is concerned with the measurement of blood pressure (BP), and more particularly with non-occlusive, passive blood pressure measurements, using a sensor of heartbeat pulses at a single site, and with a resolution sufficient to resolve Pulsus Paradoxus (PP).

Previous attempts to measure blood pressure with resolution sufficient to resolve small changes in BP associated with PP have relied on pulse propagation delay times between brachial and radial artery sites, for example. In general, such two-site approaches have only been able to track substantial changes in BP using pulse transit time (PTT) but have failed to reliably resolve the small changes in BP associated with PP.

Two-site measurement approaches have been especially deficient in the measurement of systolic variations, because the heartbeat pressure pulse changes in shape and amplitude as it heads toward the arterial periphery. These changes are due to a number of factors, including changes in the arterial wall material composition that affect the wall's elastic behavior, the taper of the main arterial branch, the distribution of branch lines, and pulse reflections. The result is that the pulse steepens and contracts as it propagates, as linear pulse propagation models predict. Additionally, non-linear effects in the arterial tree can produce pulse steepening. More importantly, the non-linear elastic response of the arterial wall results in a distinctly non-linear relationship of pulse propagation velocity and pressure.

BRIEF DESCRIPTION OF THE INVENTION

An object of the present invention is to avoid problems and disadvantages of multiple-site blood pressure measurements and to provide single-site measurement of blood pressure with less complexity and lower cost than has heretofore been possible.

More particularly, the present invention avoids the problems due to different pressure-induced pulse-shape modulations associated with different pulse detection sites, by detection of single heartbeat pulses at a single site and by analysis of individual pulses. In its preferred form, the present invention makes use of the fact that changes in time delay between different parts of a heartbeat pulse, subjected to different arterial pressures, reflect changes in blood pressure.

More particularly, it has been discovered that the well known pressure-velocity relationship that has been shown to hold for pressure-change induced pulse propagation changes also holds for the components of a single pulse, and are resolvable, since the pulse time evolution is comparatively slow. While the pressure pulse traverses the distance between brachial and radial pulse sites in time scales on the order of 40 to 50 milliseconds, the rise time of the pressure pulse, its "fastest" feature, is on the order of 100 milliseconds. As the pulse steepens and its components contract in time, as the pressure rises, time delay measurements on the rising edge of the pulse can be used to track pulse pressure changes. By measuring delay times between certain percentages of a given pulse's full amplitude (peak), automatic normalization is achieved, allowing comparison of all pulses, largely independent of coupling efficiency, which is the bane of prior pressure measurements, and which requires frequent occlusive re-calibration.

BRIEF DESCRIPTION OF THE DRAWINGS

The invention will be further described in conjunction with the accompanying drawings, which illustrate preferred (best mode) embodiments, and wherein:

FIG. 1 is a block diagram of an apparatus for implementing the invention;

FIG. 2 shows a heartbeat pulse and certain percentages of the full amplitude (pulse peak);

FIGS. 3A and 3B are a single-pulse BP determination flow chart;

FIG. 4 shows a raw data stream;

FIG. 5 shows a filtered data stream;

FIG. 6 shows zero-crossing detection;

FIG. 7 shows slope values obtained for points about each zero-crossing;

FIG. 8 shows an onset slope of a heartbeat pulse;

FIG. 9 shows interbeat interval and systolic delay-time-derived BP evolution;

FIG. 11 shows a heartbeat pulse with back-end time delay analysis;

FIG. 12 shows evolution of delay time for back-end analysis;

FIG. 13 shows interbeat interval and delay time evolution for back-end analysis;

FIG. 14 shows an overlay of systolic BP evolutions measured using the invention and a Colin Pilot BP monitor;

FIG. 15 shows evolution of averaged delay time for a series of percentiles;

FIG. 16 shows derived delay pressure as well as interbeat interval; and

FIG. 17 shows filtered Pulsus Paradoxus component for measurements using the invention and also the Colin Pilot.

DETAILED DESCRIPTION OF THE INVENTION

FIG. 1 illustrates an apparatus for implementing the invention, including a sensor 10 linked to a computer 12 (or other appropriate device) having a display 14. The sensor detects heartbeat pulses at a single site (such as the wrist) on a body through which blood flows. Analysis performed by the computer determines delay times between predetermined points on each heartbeat pulse, and the delay times are used by the computer to obtain a measurement of blood pressure. Various outputs from the computer (later described) can be viewed on the display and recorded.

In a preferred embodiment, systolic blood pressure is determined by measuring delay times between a reference point on the onset slope of the heartbeat pulse, located, for example, at 50% of the full amplitude (peak) of the heartbeat pulse, and points on the onset slope that are located at predetermined percentages of the pulse peak. FIG. 2 shows the profile of a heartbeat pulse and shows percentage points on the onset slope between the pulse onset and the pulse peak.

The present invention may use any appropriate sensor for detecting heartbeat pulses at a single site. For example, the sensor may be of the fiber-optic type disclosed in U.S. Pat. No. 6,463,187 granted Oct. 8, 2002, which responds to radial artery displacements at the wrist. In one embodiment of the invention, a completely integrated wireless sensor unit is employed featuring a fiber-optic sensor, 16-bit analog digital conversion at 512 Hz, amplification, a digital transmission system operating at 916.5 Mhz with a raw data rate of 250 Kbps using Manchester encoding, as well as an on-board Microchip PIC16C67 (OTP Version) operating at 20 MHz. This unit communicates with a PC computer via an antenna that is plugged into a serial port. It is apparent that the invention is not limited to such a sensor unit.

Figure 3A:
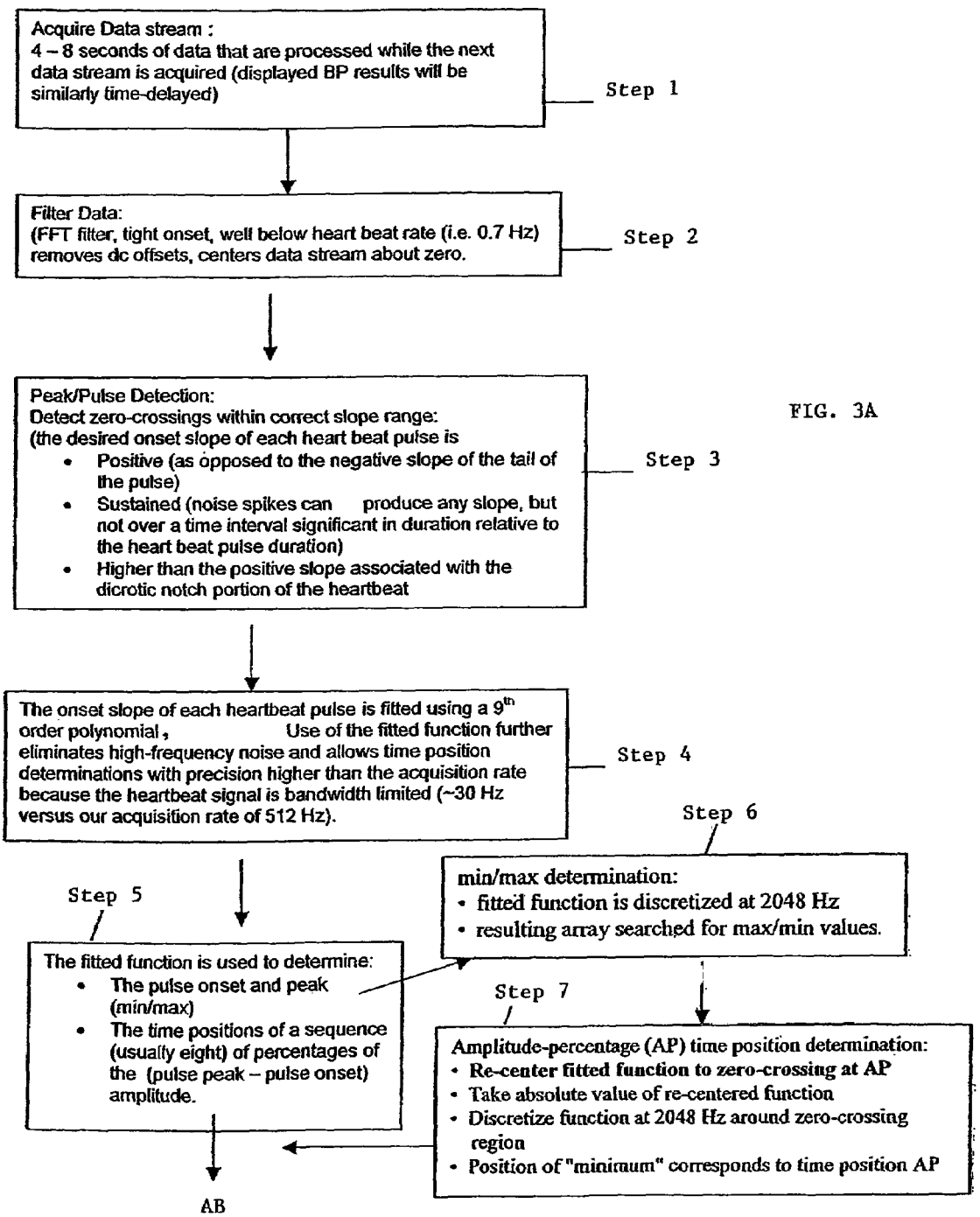

FIGS. 3A and 3B show a single-pulse BP determination flow chart in accordance with an embodiment of the invention. This embodiment is merely an example of the manner in which the invention can be implemented and is not intended to limit the invention.

Referring to FIG. 3A, a heartbeat pulse data stream is acquired for a given period of time, such as four to eight seconds, from a sensor (step 1). See FIG. 4. The acquired data stream is filtered by a fast Fourier transform filter, removing DC offsets and centering the data stream about zero (step 2). See FIG. 5. Peak/pulse detection of the filtered data is performed, in which the zero crossing of the onset slope of each heartbeat pulse is detected (step 3). See FIGS. 6 and 7. The onset slope of each heartbeat pulse is then fitted using a ninth order polynomial (step 4). See FIG. 8. While other functional forms can be used, the functional form of an arterial pulse propagation model would be preferred. The fitted function is used to determine the pulse onset and peak, and the time positions of a sequence of percentages of the full pulse amplitude (step 5). See FIG. 2. Steps 6 and 7 illustrate in detail the manner in which step 5 is performed. As shown in FIG. 3B, an effective delay time is then calculated (step 8) and is used to determine blood pressure (step 9). See FIG. 9.

The equation in step 9 has two parameters that are adjusted to fit the data, one being the exponential decay constant $\xi$, and the other a constant pressure offset C. In order to make the conversion from delay time to pressure using a velocity relationship, a distance has to be invoked, as indicated in the pressure expression. The distance, taken to be 1 meter, is not part of the fitting parameters, but simply a constant. Due to the nature of the logarithmic function, adjusting the distance accomplishes the same as adjusting the constant C; it provides a constant offset for the pressure. The scaling of the delay time to pressure is influenced solely by the choice of the exponential parameter. The values for the other constants are obtained from the literature. Specifically, $E=0.94 \cdot 10^6$ dyne/cm$^2$, h=0.08 cm, and $\alpha$=0.18 cm.

FIG. 9 conveys a sense of the degree to which Pulsus Paradoxus (PP) can be resolved with the single-point delay-time method of the invention. FIG. 9 presents the PP modulations, converted into units of pressure from the measured delay times, as well as the interbeat interval, derived from the same data stream. The peak-to-peak amplitude of the PP modulations is 7.64 mmHg (error=0.49) while the corresponding measurement with a clinical blood pressure monitor (Colin Pilot) yielded 8.08 mmHg (error=1.17).

In the embodiment just described, delay times are obtained between points on the onset slope (front-end) of the heartbeat pulse, and more particularly, systolic blood pressure is determined from such delay times.

Figure 10:
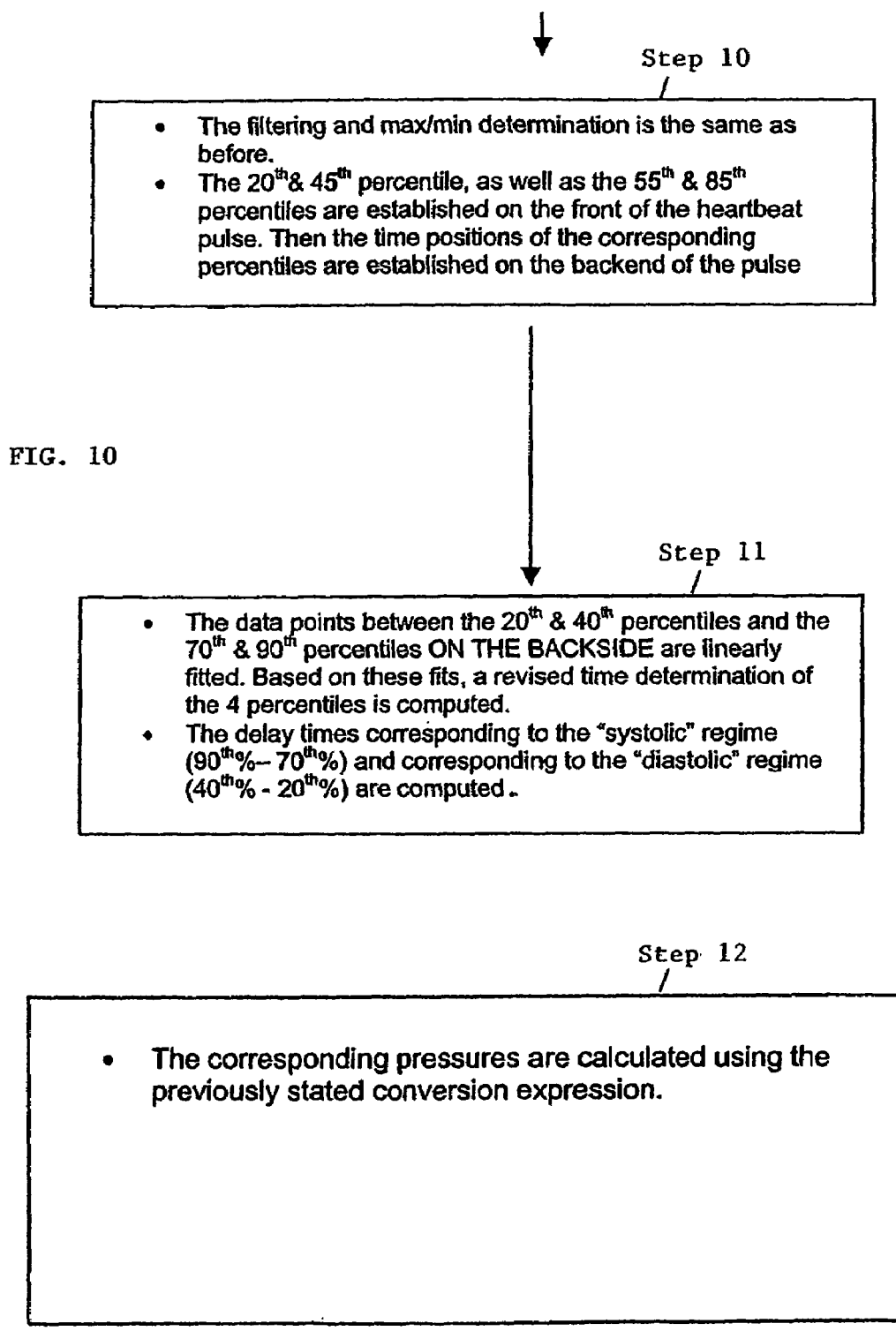
FIG. 10 is another single-pulse BP determination flow chart.

FIG. 10 is a single-pulse BP determination flowchart for measurement of both systolic and diastolic blood pressure by calculation of delay times in both systolic and diastolic regimes on the back-end of the heartbeat pulse. In this embodiment, the acquisition of a data stream, the filtering of data, and the max/min determination can be performed as in the first embodiment. Then time positions of predetermined points on the back end of the pulse are established (step 10). See FIG. 11. Data points between predetermined percentiles on the back side of the heartbeat pulse are linearly fitted, and based on these fits, a revised time determination of a predetermined number (e.g., 4) of percentiles is computed (Step 11). See FIGS. 12 and 13. Corresponding pressures are then calculated using the conversion expression used in the first flowchart (step 12). See FIG. 14. In FIG. 14, the delay time pressure obtained in accordance with the invention is the result of converting a sequence of delay time measurements between 55% and 85% of the full height of a given pulse on the falling side (back-end) of the pulse. These measurements were obtained at the wrist of a subject.

A data acquisition rate of 512 Hz, corresponding to a resolution of about 2 milliseconds, is sufficient to resolve delay time changes that are on the order of tens of milliseconds on the front-end (onset slope) of a heartbeat pulse and more by a factor of 4 to 5 on the back-end. The spectral content of the heartbeat pulse in the arterial periphery extends maximally to about 30 Hz, with the significant amplitude-carrying harmonics being in the range of up to 15–20. The heartbeat pressure is therefore bandwidth-limited, that is, except for noise interference, no spectral surprises lurk in higher frequency bands that could produce aliasing. Bearing in mind that a signal is over-sampled if the acquisition rate exceeds approximately three times the bandwidth limit, clearly then, 512 Hz over-samples the heartbeat pulse signal. With regard to establishing delay time changes that exceed the acquisition rate, it is possible to further "enhance" the acquisition rate by interpolating between measured data points during analysis.

As described earlier, one of the attributes of the invention is resolution sufficient to resolve Pulsus Paradoxus (PP). FIG. 15 shows evolution of averaged delay time for a series of percentiles on the pulse onset slope. FIG. 16 shows the results of converting the average delay time to pressure using the equation of step 9 in FIG. 3B, with an exponential factor $\xi$=0.039 and an offset of 30. The delay time pressure gives a peak-to-peak Pulsus of 6.37 mmHg with an error of 0.44 mmHg.

An interesting observation from FIG. 13 is that the artery's non-linear time-pressure relationship can be discerned. Visual comparison of the delay time modulations, presumably due to Pulsus during the first 30 seconds and the modulations during the 40–100 second period, reveals a significant difference in amplitude. This difference is essentially eliminated as the result of the non-linear conversion seen in FIG. 14. The specific values chosen to obtain the pressure conversion are $\xi$=0.027 with an offset of 72 mmHg.

With a correlation of the general BP curves established, it is interesting to compare the ability to determine PP. In order to isolate the PP modulations for comparison, both BP traces presented in FIG. 16 were Fourier filtered between 0.1 and 0.4 Hz. The results are presented in FIG. 17. In order to obtain a quantitative comparison of the magnitude of the modulations, and since the depth of the modulations did not exhibit a sustained increase or decrease, the peak-to-peak mean of all the positive and negative peak amplitudes was determined. In the case of the Colin unit, the average PP is 5.28 mmHg, with an error of 0.34 mmHg. For the invention, the corresponding values are 4.61 mmHg, with an error of 0.5 mmHg.

It is apparent that the single-site pulse delay-time method of the invention makes feasible the tracking of blood pressure changes at a resolution sufficient to determine Pulsus.

Annexed hereto are Appendices I and II showing examples of a single-point delay-time algorithm and single-point delay-time functions for implementing the invention pursuant to the above-described embodiments. It is apparent that other algorithms and functions can be used to implement the invention.

While preferred embodiments of the invention have been shown and described, it will be apparent to those skilled in the art that these embodiments are merely examples of the invention, and that various modifications can be made without departing from the principles and spirit of the invention, the scope of which is defined in the appended claims.

Single Point Delay – Time Algorithm      APPENDIX I

```
Off[General::"spell1"]
<< Graphics`
<< Graphics`MultipleListPlot`
<< Statistics`DataSmoothing`
<< NumericalMath`PolynomialFit`
```

Establish directory and read in data

```
rnum = ReadList["BODYLANBINARY.txt", Number]; // Timing
Dimensions@rnum
```

{0.771 Second, Null}

{299875}

```
rnum = Take[rnum, {1, 300000}];
```

Signal parameters (sample interval, Nyquist limit, number of samples, frequency resolution).

$$\Delta t = \frac{1}{512}; \quad \Omega = \frac{1}{2\Delta t}; \quad nn_s = \text{Dimensions}[rnum][[1]];$$

$$\Delta\omega = N\left[\frac{2\Omega}{nn_s}\right]; \quad \text{scanlengthinseconds} = N[nn_s \, \Delta t];$$

$$\{\frac{1}{\Omega}, \Delta\omega, \text{scanlengthinseconds}\} \quad (*a_{min}, a_{max}*)$$

```
Off[General::"spell1"]
<< Graphics`
<< Graphics`MultipleListPlot`
<< Statistics`DataSmoothing`
```

$\{\frac{1}{256}, 0.00170738, 585.693\}$

FFT filtering: 488 secs, bin 244 = 0.5 Hz, bin 9760 = 20 Hz

```
scanlengthinseconds * .5
scanlengthinseconds * 20
```

292.847

11713.9

```
timescale = Range[0, scanlengthinseconds, Δt];
timescale = Drop[timescale, -1];

rnumfilt = FourierFilterFunction[rnum, 292, 11713]; // Timing
```

{8.152 Second, Null}

Calculate table of zero crossings

```
DataLength = nn_s - 500;
skip = 2;
radcrossings = ZeroCrossing[Take[rnumfilt, DataLength + skip], DataLength, skip];
```

14

Single Point Delay - Time Algorithm

```
Dimensions@radcrossings
Dimensions@radslopelist
```

`{936}`

`{936}`

For each zero-crossing, calculate the slope for a data window around the zero-crossing

```
Unset[FitSlope];
radcrossdimension = Dimensions@radcrossings
radslopelist = Table[FitSlope[rnumfilt, radcrossings, n, 3],
    {n, 1, radcrossdimension[[1]]}]; // Timing
```

`{1302}`

`{0.311 Second, Null}`

Eliminate zero-crossings corresponding to low-amplitude slopes

```
{{radslopelist}, {radcrossings}} = KillPoorSlopes[radcrossings, radslopelist, 100];
Dimensions@radcrossings
```

`{563}`

Test of overlap between selected onset slopes and functional fit

```
windowstart = 50;
windowend = 550;
acquisitionrate = 512;
n = 319;
{Fitfunction, coeffs, chierror} = FitPulseOnset[rnumfilt,
     acquisitionrate, radcrossings, n, windowstart, windowend]; // Timing
functionplot = Plot[Fitfunction, {x, 0, (windowstart + windowend) / acquisitionrate},
    DisplayFunction → Identity];
f1stderiv = ∂_x Fitfunction;
function2plot =
  Plot[3 * f1stderiv, {x, 0, (windowstart + windowend) / acquisitionrate}];
DataSection = Take[rnumfilt,
    { radcrossings[[n]] - windowstart, radcrossings[[n]] + windowend}];
timebaseddata = Table[{i / acquisitionrate, DataSection[[i]]},
    {i, windowstart + windowend + 1}];
dataplot = ListPlot[timebaseddata, PlotJoined → False,
    DisplayFunction → Identity, AspectRatio → 1 / 4, ImageSize → 800];
Show[dataplot, functionplot, DisplayFunction → $DisplayFunction]
```

`{0.11 Second, Null}`

- Graphics -

Single Point Delay - Time Algorithm

```
windowstart = 50; windowend = 100; datawindowstart = 50; datawindowend = 10000;
acquisitionrate = 512;
n = 320;
{Fitfunction, coeffs, chierror} = FitPulseOnset[rnumfilt,
    acquisitionrate, radcrossings, n, windowstart, windowend]; // Timing
functionplot2 = Plot[Fitfunction, {x, 0, (windowstart + windowend) / acquisitionrate},
    DisplayFunction → Identity, PlotStyle → {Thickness[.01]}];
f1stderiv = ∂_x Fitfunction;
function2plot2 = Plot[f1stderiv,
    {x, 0, (windowstart + windowend) / acquisitionrate}, PlotStyle → {Thickness[.01]}];
DataSection = Take[rnumfilt, { radcrossings[[n]] - datawindowstart,
    radcrossings[[n]] + datawindowend}];
timebaseddata = Table[{i / acquisitionrate, DataSection[[i]]},
    {i, datawindowstart + datawindowend + 1}];
dataplot2 = ListPlot[timebaseddata, PlotJoined → True,
    DisplayFunction → Identity, AspectRatio → 1 / 4, PlotRange → All];
Show[dataplot2, functionplot2, DisplayFunction → $DisplayFunction, ImageSize → 800]

{0.03 Second, Null}

- Graphics -
```

Test of descending delay time determination on selected zero-crossings

Single Point Delay - Time Algorithm

```
n = 299;      windowstart = 50; windowend = 100;
functionstart = 0;    functionend = 0.25;
(*DescendingDelayFits[data_, acquisitionrate_, crossingtable_, n_,windowstart_,
    windowend_,functionwindowstart_, functionwindowend_,onsetpercentage1_,
    onsetpercentage2_, onsetpercentage3_, onsetpercentage4_]*)
Timing[
  {percentposition1, percentposition2, percentposition3,
      percentposition4, xc, descendingtime1, descendingfitposition1,
      descendingtime2, descendingfitposition2, descendingtime3,
      descendingfitposition3, descendingtime4, descendingfitposition4,
      xc, bottomdescendslopefit, bottomdescenderror, topdescendslopefit,
      topdescenderror, xc, pulsepeakvalue, pulseminvalue} =
    DescendingDelayFits[rnumfilt, 512, radcrossings, n, windowstart,
      windowend, functionstart, functionend, .1, .4, .7, .85];
]
{percentposition1, percentposition2, percentposition3, percentposition4,
  xc, descendingtime1, descendingfitposition1, descendingtime2,
  descendingfitposition2, descendingtime3, descendingfitposition3, descendingtime4,
  descendingfitposition4, xc, bottomdescendslopefit, bottomdescenderror,
  topdescendslopefit, topdescenderror, "xxx", pulsepeakvalue, pulseminvalue}
{"top delay time ", descendingfitposition3 - descendingfitposition4,
  " bottom delay time ", descendingfitposition1 - descendingfitposition2,}

{0.11 Second, Null}

{0.07375, 0.0994, 0.12315, 0.14025, xxx, 0.672969, 0.674922, 0.305781,
  0.307734, 0.255, 0.256953, 0.237422, 0.239375, xxx, 736.973 - 7.95716 x,
  6.37441, 1755.22 - 69.517 x, 0.00040977, xxx, 2267.75, -1674.53}

{top delay time , 0.0175781, bottom delay time , 0.367188, Null}
```

Test of onset delay time determination on selected zero-crossings

```
      jj = 403;   windowstart = 50; windowend = 100;
functionstart = 0;    functionend = 0.25;

crossingtable = radcrossings;
crossingtablelength = Dimensions@crossingtable;
        {percentposition1, percentposition2, percentposition3,
  percentposition4, xc, percentposition5, percentposition6,
  percentposition7, percentposition8, xc, pulsepeakvalue, pulseminvalue} =
  OnsetDelays[rnumfilt, 512, crossingtable, jj, windowstart, windowend,
    functionstart, functionend, .1, .4, .5, .6, .7, .8, .9, .95]
percentposition8 - percentposition1

{0.07745, 0.10215, 0.10975, 0.11735, xxx,
  0.1259, 0.1354, 0.1487, 0.15915, xxx, 5647.33, -3796.62}

0.0817
```

Processing of all heart beats in the zero-crossing table. Delay times are stored in eight separate tables.

Single Point Delay - Time Algorithm

```
        windowstart = 50; windowend = 100;
functionstart = 0;   functionend = 0.25;
Timing[
 crossingtable = radcrossings;
 For[crossingtablelength = Dimensions@crossingtable;

percent1array = {};
    percent2array = {};
    percent3array = {};
    percent4array = {};
    percent5array = {};
    percent6array = {};
    percent7array = {};
    percent8array = {};
    modifiedcrossingtable = {};

jj = 4, jj < crossingtablelength[[1]] -1, jj++,
      {percentposition1, percentposition2, percentposition3,
   percentposition4, xc, percentposition5, percentposition6,
   percentposition7, percentposition8, xc, pulsepeakvalue, pulseminvalue} =
   OnsetDelays[rnumfilt, 512, crossingtable, jj, windowstart, windowend,
   functionstart, functionend, .2, .4, .5, .6, .7, .8, .9, .95];

percent1array = AppendTo[percent1array, percentposition1];
    percent2array = AppendTo[percent2array, percentposition2];
    percent3array = AppendTo[percent3array, percentposition3];
    percent4array = AppendTo[percent4array, percentposition4];
    percent5array = AppendTo[percent5array, percentposition5];
    percent6array = AppendTo[percent6array, percentposition6];
    percent7array = AppendTo[percent7array, percentposition7];
    percent8array = AppendTo[percent8array, percentposition8];
    modifiedcrossingtable =
  AppendTo[modifiedcrossingtable, crossingtable[[jj]]];
    ];
]
{72.013 Second, Null}
```

Observersations: For the top delay the 50, 95% yielded the best results. 95%, as opposed to 90%, made a significant difference. Extending the range downward reduces the strength of the pulsus modulations relative to the large-scale changes due to the valsalva episodes. It also enlarges the time delays, making the whole spectrum cleaner. The 2nd and 3rd episodes are well resolved; the first not very well.

Single Point Delay - Time Algorithm storage and retrieval of calculated delay times

```
{percent1array, percent2array, percent3array,
    percent4array, percent5array, percent6array, percent7array,
    percent8array, modifiedcrossingtable} >> "arraystorage.txt";
```

```
<< "arraystorage.txt";
{percent1array, percent2array, percent3array, percent4array, percent5array,
    percent6array, percent7array, percent8array, modifiedcrossingtable} = %;
``` weighting factors and calculation of weighting factor sum

```
w8 = 2; w7 = 2; w6 = 4; w5 = 4; w4 = 4; w3 = 2; w2 = 1;
wsum = w8 + w7 + w6 + w5 + w4 + w3 + w2;
```

```
w8 = 2; w7 = 2; w6 = 1; w5 = 1; w4 = 1; w3 = 1; w2 = 1;
wsum = w8 + w7 + w6 + w5 + w4 + w3 + w2;
``` calculation of effective delay time

```
averagedelay = ((percent8array - percent1array) w8 +
    (percent7array - percent1array) w7 + (percent6array - percent1array) w6 +
    (percent5array - percent1array) w5 + (percent4array - percent1array) w4 +
    (percent3array - percent1array) w3 + (percent2array - percent1array) w2) / wsum;
```

```
averagedelay[[317]]
```

-0.0325386 graph of delay time

Single Point Delay - Time Algorithm

```
filteredTT = FourierFilterFunction[Abs[averagedelay], 0, 150];
ListPlot[Transpose[{modifiedcrossingtable/512, filteredTT}], PlotJoined → True,
 AspectRatio → 1/4, GridLines → Automatic, PlotRange → {{140, 180}, {0.03, .05}}]
```

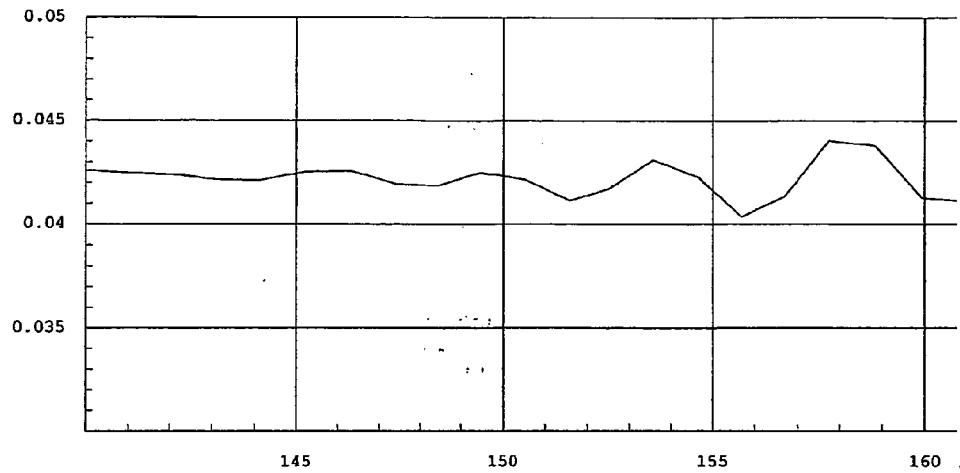

- Graphics -

Calculation of delay time-based pressure

```
pressureabs = Abs[pressure[.039, MovingAverage[Abs[averagedelay], 3], 30]];
```

```
filteredPP = FourierFilterFunction[pressure[.039, Abs[averagedelay], 35], 0, 150];
ListPlot[Transpose[{modifiedcrossingtable/512, filteredPP}], PlotJoined → True,
 AspectRatio → 1/4, GridLines → Automatic, PlotRange → {{140, 180}, {100, 130}}]
```

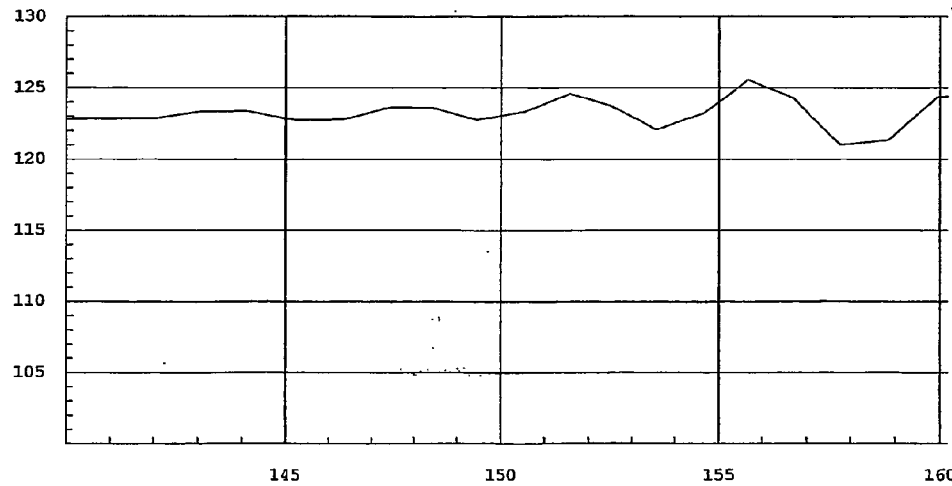

- Graphics -

Single Point Delay - Time Algorithm

```
ListPlot[Transpose[{modifiedcrossingtable/512, interbeatinterval}],
  PlotJoined → True, AspectRatio → 1/4,
  GridLines → Automatic, PlotRange → {{140, 180}, {.8, 1.2}}]
```

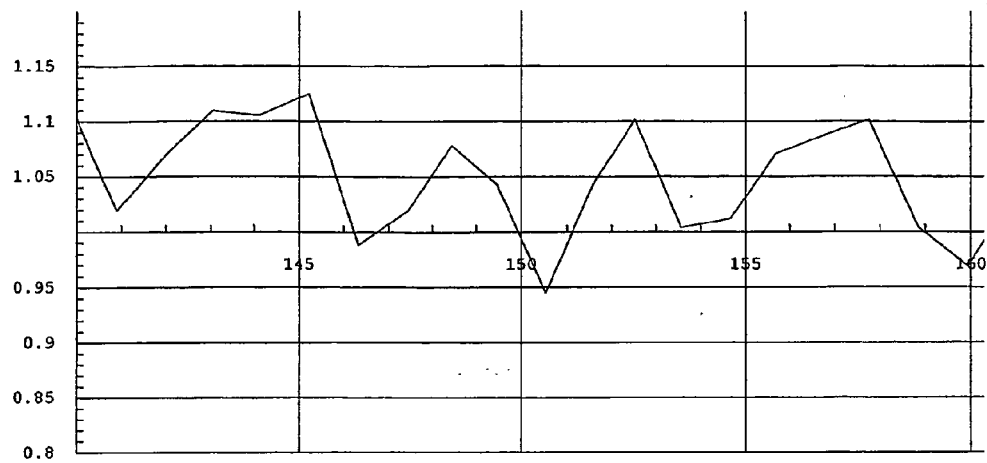

- Graphics -

Comparison of delay time evolution and interbeat interval

```
filteredPP = FourierFilterFunction[pressure[.039, Abs[averagedelay], 35], 0, 150];
ListPlot[Transpose[{modifiedcrossingtable/512, filteredPP}], PlotJoined → True,
  AspectRatio → 1/4, GridLines → Automatic, PlotRange → {{520, 570}, {105, 130}}]
```

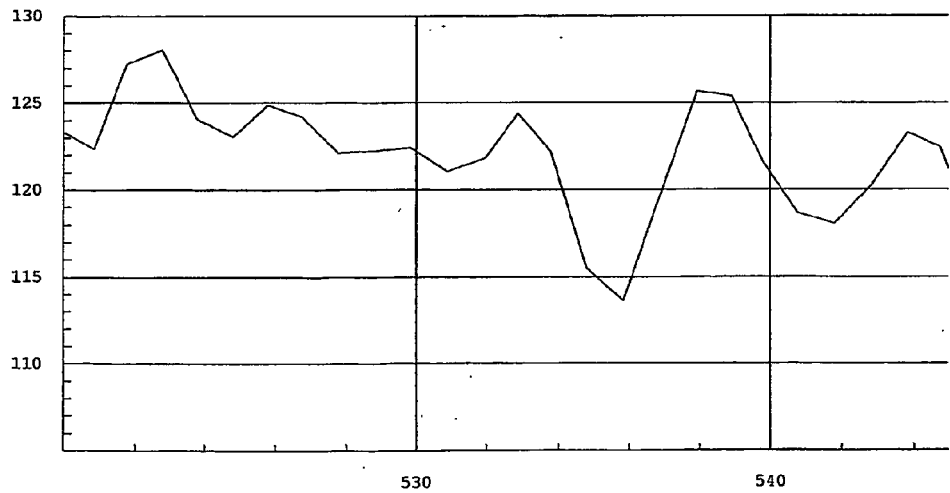

- Graphics - calculation of interbeat interval

```
onelesscrossing = Drop[radcrossings, 1];
interbeatinterval = N[(onelesscrossing - Drop[radcrossings, -1]) * Δt];
```

Single Point Delay - Time Algorithm

```
ListPlot[Transpose[{modifiedcrossingtable/512, interbeatinterval}],
   PlotJoined → True, AspectRatio → 1 / 4,
   GridLines → Automatic, PlotRange → {{522, 572}, {.8, 1.2}}]
```

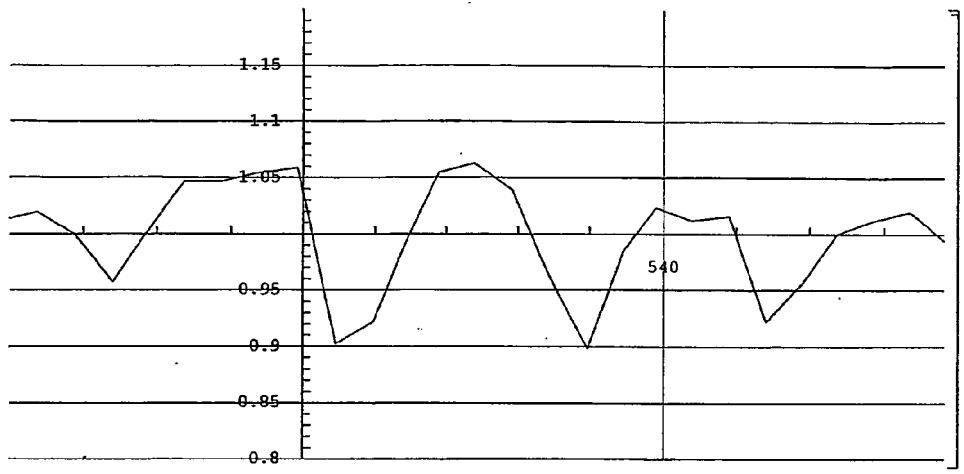

- Graphics -

Function calls for saving parameters to file

```
SaveDataToFile["MCBdescendfitdelays.txt", radcrossings,
   "radcrossings", interbeatinterval, "interbeatinterval",
   descendtopdelayarray, "descendtopdelayarray", descendbottomdelayarray,
   "descendbottomdelayarray", descendtopchisquared, "descendtopchisquared",
   descendbottomchisquared, "descendbottomchisquared",
   radslopelist, "radslopelist", radslopelist, "radslopelist"]
``` radcrossings{407}interbeatinterval{406}descendtopdelayarray{402}descendbottomdelayarray{402}
descendtopchisquared{402}descendbottomchisquared{402}radslopelist{411}radslopelist{411}

```
SaveDataToFile["MCBcrosspulseresults2090.dat", radcrossings,
   "radcrossings", descendmaxarray, "descendmaxarray", interbeatinterval,
   "interbeatinterval", peakdelayarray, "peakdelayarray",
   descendminarray, "descendminarray", lowdelayarray, "lowdelayarray",
   radslopelist, "radslopelist", radslopelist, "radslopelist"]
``` radcrossings{403}descendmaxarray{400}interbeatinterval{402}peakdelayarray
{400}descendminarray{400}lowdelayarray{400}radslopelist{403}radslopelist{403}

Single Point Delay - Time Functions                              APPENDIX II

```
<< Statistics`LinearRegression`
<< NumericalMath`InterpolateRoot`
```

Zerocrossing is passed the inputdata and the length of the inputdata (range). The function returns a table of the positions (within the skipinterval) of the zero crossings.

```
ZeroCrossing[inputdata_, range_, skipinterval_] :=
  Module[{crossingtable, m, i},
    For[crossingtable = {0};
        i = 0, i < range, i = i + skipinterval,
      If[
        inputdata[[i]] > 0,
          If[
              inputdata[[i + skipinterval]] < 0,
              AppendTo[crossingtable, i];
              ],
          If[
              inputdata[[i + skipinterval]] > 0,
              AppendTo[crossingtable, i];
              ]
        ]
      ];
    crossingtable = Drop[crossingtable, 1];
    crossingtable = Flatten@crossingtable;
    crossingtable]
```

FourierFilterFunction accepts the input data, the cutonbin and the cutoffbin of the filter, and returns the filtered data. *Mathematica* FFT array runs from 1 to n

Single Point Delay - Time Functions

```
FourierFilterFunction[inputdata_, cutonbin_, cutoffbin_] :=
 Module[{fftlength, fft, j, invfft},
  fft = Fourier[inputdata];
  For[fftlength = Dimensions@fft;
   j = 1, j < cutonbin + 1, j++,
   fft[[j]] = 0;
  ];
  For[
   j = cutoffbin + 2, j < fftlength[[1]] - cutoffbin + 1, j++,
   fft[[j]] = 0;
  ];
  For[
   j = fftlength[[1]] - cutonbin + 2, j < fftlength[[1]] + 1, j++,
   fft[[j]] = 0;
  ];
  invfft = InverseFourier[fft];
  invfft]
```

KillPoorSlopes wipes out points in the crossingtable & slopelist with slopes below the absolute value of a slope threshold. Returns two arrays. For negative signals: slopelist[[i]] > slopethreshold

```
KillPoorSlopes[crossingtable_, slopelist_, slopethreshold_] :=
 Module[{izero, i, modifiedcrossingtable,
   killslopelist, modifiedslopelist, listlength},
  For[listlength = Dimensions@crossingtable;
   killslopelist = {0};
   modifiedcrossingtable = crossingtable;
   i = 1, i < listlength[[1]], i++,
     If[
      slopelist[[i]] < slopethreshold,
       killslopelist = AppendTo[killslopelist, {i}];
     ]
  ];
  killslopelist = Drop[killslopelist, 1];
  killslopelist = Reverse@killslopelist;
  modifiedslopelist = Delete[slopelist, killslopelist];
  modifiedcrossingtable = Delete[crossingtable, killslopelist];
  {{modifiedslopelist}, {modifiedcrossingtable}}]
```

FindPeakCenterPosition receives position and value arrays of pulse onset and pulse peak and returns an array of the amplitude center position based on averaging before & after peak values.

Single Point Delay – Time Functions

```
FindPeakCenterPosition[beforepeakposition_, beforepeakvalue_,
    afterpeakposition_, afterpeakvalue_, pulsedata_] :=
Module[{averagevalue, minimum, maxindex, minindex,
    crossingtablelength, minindexarray, m, i, datasection, minarray},
    For[crossingtablelength = Dimensions@beforepeakposition;
        minindexarray = {};
        minarray = {};
        datasection = {};
        differential = {};
        i = 1, i < crossingtablelength[[1]] + 1, i++,
            datasection =
    Take[pulsedata, {beforepeakposition[[i]], afterpeakposition[[i]]}];
            averagevalue = (afterpeakvalue[[i]] + beforepeakvalue[[i]]) / 2;
            differential = Abs[datasection - averagevalue];
            minimum = Min[differential];
            minindex = Flatten[Position[differential, minimum]][[1]];
            minarray = AppendTo[minarray, minimum];
            minindexarray =
    AppendTo[minindexarray, beforepeakposition[[i]] + minindex];
        ];
        minindexarray]
```

KillZerosInList scans list up to first zero, then wipes out rest of list

```
KillZerosInList[crossingtable_] :=
    Module[{izero, i, modifiedcrossingtable},
        For[listlength = Dimensions@crossingtable;
            izero = 0;
            i = 1, i < listlength[[1]], i++,
                If[
                    crossingtable[[i]] == 0,
                    izero = i;
                    i = listlength;
                ]
            ];
        If[izero > 0,
            modifiedcrossingtable =
                Drop[crossingtable, -(listlength[[1]] - izero + 1)],
            modifiedcrossingtable = crossingtable;
        ];
        modifiedcrossingtable]
```

NormalSection accepts the order of the crossing, the table of zero-crossing positions, and the input data. The function returns 500 points about the specified crossing, normalized to 1.

Single Point Delay - Time Functions

```
NormalSection[n_, crossingtable_, data_, windowstart_, windowend_] :=
  Module[{Section, SectionMax, SectionMin, NormalizedSection},
    Section = Table[0, {j, windowstart + windowend}];
    Section = Take[data,
        { crossingtable[[n]] - windowstart, crossingtable[[n]] + windowend}];
    SectionMax = Max[Section];
    SectionMin = Min[Section];
    NormalizedSection = (Section - SectionMin) / (SectionMax - SectionMin);
    NormalizedSection]
```

FitSlope accepts the data array, the crossing table, and the crossing order, and returns the slope coefficient of a quadratic fit for + - "range" points about crossing

```
FitSlope[data_, crossingtable_, n_, range_] :=
  Module[{datafit, slope, nextcoeff},
        datafit = Fit[Take[data,
            { crossingtable[[n]] - range, crossingtable[[n]] + range}], {1, x, x^2}, x];
        slope = Coefficient[datafit, x];
        nextcoeff = Coefficient[datafit, x^2];
        slope]
```

FitSlopeArray accepts the data array, the crossing table, and returns arrays of the slope coefficient and the 2nd coefficient of a quadratic fit for + - "range" points about crossing

```
FitSlopeArray[data_, crossingtable_, range_] :=
  Module[{datafit, slope, nextcoeff,
      slopearray, nextcoeffarray, crossingtablelength},
    For[crossingtablelength = Dimensions@crossingtable;
        slopearray = {};
        nextcoeffarray = {};
        i = 2, i < crossingtablelength[[1]], i++,
            datafit = Fit[Take[data,
            { crossingtable[[i]] - range, crossingtable[[i]] + range}], {1, x}, x];
            slope = Coefficient[datafit, x];
            nextcoeff = Coefficient[datafit, x];
            slopearray = AppendTo[slopearray, slope];
            nextcoeffarray = AppendTo[nextcoeffarray, nextcoeff];
        ];
    {slopearray, nextcoeffarray}]
```

FitPulseOnset accepts the data, the ACQUISITION RATE, the zero-crossing table, and the order of the crossing and returns the coefficients of a 9th order fit about the crossing over a variable data window Single Point Delay - Time Functions

```
FitPulseOnset[data_, acquisitionrate_,
    crossingtable_, n_, windowstart_, windowend_] :=
  Module[{FitFunction, ChiSquared, DataSection, ChiSquareArray,
      FunctionValue, lengthofDataSection, timebaseddata},
    lengthofDataSection = windowstart + windowend;
    DataSection = Take[data,
      { crossingtable[[n]] - windowstart, crossingtable[[n]] + windowend}];
    timebaseddata = Table[{i / acquisitionrate, DataSection[[i]]},
      {i, lengthofDataSection + 1}];
    {FitFunction, Fitcoeffs, ChiSquared} =
      Regress[timebaseddata, Table[x^i, {i, 0, 9}], x,
        RegressionReport → {BestFit, BestFitParameters, RSquared}];
    {FitFunction[[2]], Fitcoeffs[[2]], ChiSquared[[2]]}]
```

PulseOnsetTurningPoints accepts the data, the ACQUISITION RATE, the zero-crossing table, and the order of the crossing, calls FitPulseOnset to get the appropriate pulse onset fit and, using the 3rd derivative (which has zeros at the turning points), determines both turning points RELATIVE TO THE CROSSING in SECONDS, and returns them in proper format

```
PulseOnsetTurningPoints[data_, acquisitionrate_,
    crossingtable_, n_, windowstart_, windowend_] :=
  Module[{ThirdDerivFunction, TurningPoint1,
      TurningPoint2, ffunction, fitcoeff, chierror},
    {ffunction, fitcoeff, chierror} = FitPulseOnset[data,
      acquisitionrate, crossingtable, n, windowstart, windowend];
    ThirdDerivFunction = 6 fitcoeff[[4]] + 24 fitcoeff[[5]] x +
      60 fitcoeff[[6]] x^2 + 120 fitcoeff[[7]] x^3 + 210 fitcoeff[[8]] x^4 +
      336 fitcoeff[[9]] x^5 + 504 fitcoeff[[10]] x^6;
```

$$TurningPoint1 = -\frac{windowstart}{acquisitionrate} + x /.$$

FindRoot[ (ThirdDerivFunction) == 0, {x, .04}];

$$TurningPoint2 = -\frac{windowstart}{acquisitionrate} + x /.$$

FindRoot[ (ThirdDerivFunction) == 0, {x, .12}];

{ThirdDerivFunction, TurningPoint1, TurningPoint2, chierror}]

FunctionPeakFinderDiscrete accepts the function and the range window, and the stepsize for searching. It generates a table and finds the max/min values of the array and returns their positions & values in time relative to the range window.

Single Point Delay – Time Functions

```
FunctionPeakFinderDiscrete[
    fitfunction_, startwindow_, endwindow_, stepsize_] :=
Module[{functionmaximum, functionminimum, rootarraydimension, a,
    functionevalarray, dummyfitfunction, minposition, maxposition},
  a = {};
  dummyfitfunction[y_] = fitfunction /. x -> y;
  a = Range[startwindow, endwindow, (endwindow - startwindow) / stepsize] // N;
  functionevalarray = dummyfitfunction[#] & /@ a;
  functionmaximum = Max[functionevalarray];
  functionminimum = Min[functionevalarray];
  maxposition = Position[functionevalarray, functionmaximum];
  minposition = Position[functionevalarray, functionminimum];
  {minposition[[1]][[1]] * (endwindow - startwindow) / stepsize,
    functionminimum, maxposition[[1]][[1]] *
    (endwindow - startwindow) / stepsize, functionmaximum}]
```

FunctionPeakFinder accepts the function, the range window, and +1 for positive peaks (-1 for negative), looks fo 7 zero-crossings in the derivative of the function, and returns the highest/lowest peak (ONE (x,y) PAIR ONLY)

```
FunctionPeakFinder[fitfunction_,
    startwindow_, endwindow_, positiveORnegativePeak_] :=
Module[{functionderivative, derivroots, peakvalue,
    rootsdummy, peaksdummy, jpeak, rootarraydimension},
  derivroots = {};
  functionderivative = ∂_x fitfunction;
  rootsdummy = x /.
    FindRoot[ (functionderivative) == 0, {x, startwindow}, MaxIterations -> 50];
  If[startwindow < rootsdummy < endwindow,
    derivroots = AppendTo[derivroots, rootsdummy]]
  Clear[rootsdummy];
  rootsdummy =
    x /. FindRoot[ (functionderivative) == 0, {x, (startwindow + endwindow) / 8},
      MaxIterations -> 50, DampingFactor -> .25];
  If[startwindow < rootsdummy < endwindow,
    derivroots = AppendTo[derivroots, rootsdummy]]
  Clear[rootsdummy];
  rootsdummy =
    x /. FindRoot[ (functionderivative) == 0, {x, (startwindow + endwindow) / 7},
      MaxIterations -> 50, DampingFactor -> .25];
  If[startwindow < rootsdummy < endwindow,
    derivroots = AppendTo[derivroots, rootsdummy]]
  Clear[rootsdummy];
  rootsdummy =
    x /. FindRoot[ (functionderivative) == 0, {x, (startwindow + endwindow) / 6},
      MaxIterations -> 50, DampingFactor -> .25];
  If[startwindow < rootsdummy < endwindow,
    derivroots = AppendTo[derivroots, rootsdummy]]
```

Single Point Delay - Time Functions

```
Clear[rootsdummy];
rootsdummy =
  x /. FindRoot[ (functionderivative) == 0, {x, (startwindow + endwindow) / 4},
      MaxIterations → 50, DampingFactor → .25];
If[startwindow < rootsdummy < endwindow,
    derivroots = AppendTo[derivroots, rootsdummy]]
Clear[rootsdummy];
rootsdummy =
  x /. FindRoot[ (functionderivative) == 0, {x, (startwindow + endwindow) / 2},
      MaxIterations → 50, DampingFactor → .25];
If[startwindow < rootsdummy < endwindow,
    derivroots = AppendTo[derivroots, rootsdummy]]
Clear[rootsdummy];
rootsdummy =
  x /. FindRoot[ (functionderivative) == 0, {x, 3 * (startwindow + endwindow) / 4},
      MaxIterations → 50, DampingFactor → .25];
If[startwindow < rootsdummy < endwindow,
    derivroots = AppendTo[derivroots, rootsdummy]]
Clear[rootsdummy];
rootsdummy = x /. FindRoot[ (functionderivative) == 0,
    {x, endwindow}, MaxIterations → 50, DampingFactor → .25];
If[startwindow < rootsdummy < endwindow,
    derivroots = AppendTo[derivroots, rootsdummy]]
 For[peakvalue = 0;
      jpeak = 0;
      rootarraydimension = Dimensions@derivroots;
   j = 1, j < rootarraydimension[[1]] + 1, j++,
      peaksdummy = fitfunction /. x → derivroots[[j]];
   If[positiveORnegativePeak < 0, If[peaksdummy < peakvalue,
      peakvalue = peaksdummy;
      jpeak = j]]
   If[positiveORnegativePeak > 0, If[peaksdummy > peakvalue,
      peakvalue = peaksdummy;
      jpeak = j]]
  ];
 {derivroots[[jpeak]], peakvalue}]
```

AllPulseOnsetMaxSlopes uses FitPulseOnset and FunctionPeakFinder to fit the pulse onset and then determine the magnitude and location of the maximum slope on the pulse onset.

Single Point Delay - Time Functions

```
AllPulseOnsetMaxSlopes[data_, acquisitionrate_,
   crossingtable_, windowstart_, windowend_] :=
 Module[{slopeposition, slopemax, slopemaxpositionarray,
     slopemaxarray, derivfunction, crossingtablelength, thirdderiv},
   For[crossingtablelength = Dimensions@crossingtable;
       slopemaxpositionarray = {};
       slopemaxarray = {};
       chierrorarray = {};
    jj = 1, jj < crossingtablelength[[1]] + 1, jj++,
         {Fitfunction, coeffs, chierror} = FitPulseOnset[data,
       acquisitionrate, crossingtable, jj, windowstart, windowend];
         derivfunction = ∂ₓ Fitfunction;
         {slopeposition, slopemax} =
   FunctionPeakFinder[derivfunction, .08, .18, 1];
         slopemaxpositionarray =
   AppendTo[slopemaxpositionarray, slopeposition];
         slopemaxarray = AppendTo[slopemaxarray, slopemax];
       ];
    {slopemaxpositionarray, slopemaxarray, chierror}]
```

PercentofAmplitudePoints determines the time position of selected amplitude percentages, relative to truecenter. uses FitPulseOnset and PulseOnsetTurningPoints to find turning point pairs for all pulse onsets identified in the crossingtable.

```
PercentofAmplitudePoints[data_, acquisitionrate_,
    crossingtable_, n_, windowstart_, windowend_, functionwindowstart_,
    functionwindowend_, uppercentage_, downpercentage_] :=
  Module[{Fitfunction, coeffs, chierror, pulsepeakposition, pulsepeakvalue,
     pulseminposition, pulseminvalue, pulsecentervalue, pulsecenterposition,
     a, dummyfitfunction, functionevalminimum, minposition, functionevalarray,
     lowpercentposition, highpercentposition, zerocrossingposition},
  percentroots = {};
  a = {};
  functionevalarray = {};
  {Fitfunction, coeffs, chierror} =
           FitPulseOnset[data,
    acquisitionrate, crossingtable, n, windowstart, windowend];

(* find the max & min value positions of the pulse onset *)
  {pulseminposition, pulseminvalue, pulsepeakposition, pulsepeakvalue} =
   FunctionPeakFinderDiscrete[Fitfunction,
     functionwindowstart, functionwindowend, 100];

(* find the center position of the pulse in time *)
        pulsecentervalue = (pulsepeakvalue + pulseminvalue) / 2;
        dummyfitfunction[y_] = (Fitfunction - pulsecentervalue) /. x → y;
        a = Range[pulseminposition, pulsepeakposition,
```

Single Point Delay - Time Functions

```
      (pulsepeakposition - pulseminposition) / 150] // N;
   functionevalarray = dummyfitfunction[#] & /@ a;
   functionevalminimum = Min[Abs[functionevalarray]];
   minposition =
 Position[Abs[functionevalarray], functionevalminimum];
   pulsecenterposition = minposition[[1]][[1]] *
   (pulsepeakposition - pulseminposition) / 150 + pulseminposition;
Clear[dummyfitfunction];

(* find the zero-crossing of the pulse onset *)
   dummyfitfunction[y_] = Fitfunction /. x → y;
   functionevalarray = dummyfitfunction[#] & /@ a;
   functionevalminimum = Min[Abs[functionevalarray]];
   minposition =
 Position[Abs[functionevalarray], functionevalminimum];
   zerocrossingposition = minposition[[1]][[1]] *
   (pulsepeakposition - pulseminposition) / 150 + pulseminposition;
(* Print[pulsecenterposition]; *)
(* Print[percentroots]; *)
Clear[dummyfitfunction];

(* find the % of min value position on pulse onset *)
   dummyfitfunction[y_] =
 (Fitfunction - pulseminvalue * downpercentage) /. x → y;
   functionevalarray = dummyfitfunction[#] & /@ a;
   functionevalminimum = Min[Abs[functionevalarray]];
   minposition =
 Position[Abs[functionevalarray], functionevalminimum];
   lowpercentposition = minposition[[1]][[1]] *
   (pulsepeakposition - pulseminposition) / 150 + pulseminposition;
(* Print[pulsecenterposition]; *)
(* Print[percentroots]; *)
Clear[dummyfitfunction];

(* find the % of max value position on pulse onset *)
   dummyfitfunction[y_] =
 (Fitfunction - pulsepeakvalue * uppercentage) /. x → y;
   functionevalarray = dummyfitfunction[#] & /@ a;
   functionevalminimum = Min[Abs[functionevalarray]];
   minposition =
 Position[Abs[functionevalarray], functionevalminimum];
   highpercentposition = minposition[[1]][[1]] *
   (pulsepeakposition - pulseminposition) / 150 + pulseminposition;
(* rootsdummy =   x/.FindRoot[
   (Fitfunction-pulsepeakvalue*uppercentage)==0,
   {x, pulsepeakposition-.05, pulseminposition, pulsepeakposition}];
If[functionwindowstart<rootsdummy<functionwindowend,
```

Single Point Delay - Time Functions

```
        percentroots=AppendTo[percentroots,rootsdummy]]
     Clear[rootsdummy]; *)
  {pulsecenterposition, zerocrossingposition,
    lowpercentposition, highpercentposition, pulsepeakposition,
    pulsepeakvalue, pulseminposition, pulseminvalue}]
```

FitEntireSlope accepts the data, the zero-crossing table, and the order of the crossing, normalizes the data section, and returns a normalized fourth order fit of 450 points about the crossing

```
FitEntireSlope[data_, crossingtable_, n_, windowstart_, windowend_] :=
  Module[{FitFunction, ChiSquared,
    NormalizedDataSection, ChiSquareArray, FunctionValue},
    NormalizedDataSection = NormalSection[n,
   crossingtable, data, windowstart, windowend];
      lengthofNormSection = Dimensions@NormalizedDataSection;
      FitFunction = Fit[NormalizedDataSection, {1, x, x², x³, x⁴}, x];
      For[ChiSquared = 0;
          ChiSquareArray = {0};
          i = 100, i < lengthofNormSection[[1]] - 100, i++,
             FunctionValue = FitFunction /. x -> i;
             ChiSquared =
    ChiSquared + Abs[FunctionValue - NormalizedDataSection[[i]]]^2;
      ];
  {FitFunction, ChiSquared}]
```

SaveDataToFile files result arrays into a multicolumn file for import into spreadsheets etc

```
SaveDataToFile[outfilename_, array1_, array1label_, array2_, array2label_,
   array3_, array3label_, array4_, array4label_, array5_, array5label_,
   array6_, array6label_, array7_, array7label_, array8_, array8label_] :=
      Module[{filetable},
   Print[array1label , Dimensions@array1, array2label , Dimensions@array2,
    array3label , Dimensions@array3, array4label , Dimensions@array4,
    array5label , Dimensions@array5, array6label , Dimensions@array6,
    array7label , Dimensions@array7, array8label , Dimensions@array8];

filetable =
   TableForm[{array1, array2, array3, array4, array5, array6, array7, array8},
      TableDirections -> {Row, Column}, TableSpacing -> {1, 0},
      TableHeadings -> {{array1label , array2label, array3label, array4label,
         array5label, array6label, array7label, array8label}}];
        Export[outfilename, filetable, "Table"];
   ]
```

SaveDataToFile files result arrays into a multicolumn file for import into spreadsheets etc
BE AWARE THAT IF MATHEMATICA OUTPUTS AN ARRAY IN FRACTIONS FORMAT, THE FILE WILL UNIMPORTABLE INTO A SPREADSHEET Single Point Delay - Time Functions

```
SaveDataToFile2[outfilename_, array1_, array1label_, array2_, array2label_,
    array3_, array3label_, array4_, array4label_, array5_, array5label_] :=
        Module[{filetable},
    Print[array1label , Dimensions@array1, array2label ,
      Dimensions@array2, array3label , Dimensions@array3, array4label ,
      Dimensions@array4, array5label , Dimensions@array5];

filetable = TableForm[{array1, array2, array3, array4, array5},
        TableDirections -> {Row, Column}, TableSpacing -> {1, 0}, TableHeadings ->
          {{array1label , array2label, array3label, array4label, array5label}}];
            Export[outfilename, filetable, "Table"];
    ]
```

PairOfPercentofAmplitudePoints determines the time position of selected amplitude percentages, relative to truecenter(100% downpercentage is at the pulse onset, 100%uppercentage is at the pulse peak). Uses FitPulseOnset and PulseOnsetTurningPoints to find turning point pairs for all pulse onsets identified in the crossingtable. Then it finds the matching point on the down slope on the backend of the heartbeat pulse.

```
PairOfPercentofAmplitudePoints[data_, acquisitionrate_,
    crossingtable_, n_, windowstart_, windowend_, functionwindowstart_,
    functionwindowend_, uppercentage_, downpercentage_] :=
Module[{Fitfunction, coeffs, chierror, pulsepeakposition,
        pulsepeakvalue, pulseminposition, pulseminvalue, pulsecentervalue,
        pulsecenterposition, a, dummyfitfunction, functionevalminimum,
        functionevalmaximum, minposition, maxposition, functionevalarray,
        lowpercentposition, highpercentposition, zerocrossingposition,
        descendingmaxposition, descendingminposition, datasection, datastart,
        dataend, offsetdatasection, descendingmaxtime, descendingmintime},
    percentroots = {};
    datasection = {};
    offsetdatasection = {};
    a = {};
    functionevalarray = {};
    {Fitfunction, coeffs, chierror} =
            FitPulseOnset[data,
        acquisitionrate, crossingtable, n, windowstart, windowend];

(* find the max & min value positions of the pulse onset *)
    {pulseminposition, pulseminvalue, pulsepeakposition, pulsepeakvalue} =
      FunctionPeakFinderDiscrete[Fitfunction,
        functionwindowstart, functionwindowend, 100];

(* find the center position of the pulse in time *)
            pulsecentervalue = (pulsepeakvalue + pulseminvalue) /2;
            dummyfitfunction[y_] = (Fitfunction - pulsecentervalue) /. x -> y;
            a = Range[pulseminposition, pulsepeakposition,
        (pulsepeakposition - pulseminposition) /150] // N;
```

Single Point Delay - Time Functions

```
        functionevalarray = dummyfitfunction[#] & /@ a;
        functionevalminimum = Min[Abs[functionevalarray]];
        minposition =
  Position[Abs[functionevalarray], functionevalminimum];
        pulsecenterposition = minposition[[1]][[1]] *
    (pulsepeakposition - pulseminposition) / 150 + pulseminposition ;
Clear[dummyfitfunction];

(* find the zero-crossing of the pulse onset *)
(*       dummyfitfunction[y_]=Fitfunction/.x->y;
        functionevalarray=dummyfitfunction[#]&/@a;
        functionevalminimum=Min[Abs[functionevalarray]];
        minposition=
   Position[Abs[functionevalarray],functionevalminimum];
        zerocrossingposition=minposition[[1]][[1]]*
    (pulsepeakposition-pulseminposition)/150 +pulseminposition ;*)
(* Print[pulsecenterposition]; *)
(* Print[percentroots]; *)
Clear[dummyfitfunction];

(* find the % of min value position on pulse onset *)
        dummyfitfunction[y_] =
 (Fitfunction - pulseminvalue * downpercentage) /. x -> y;
        functionevalarray = dummyfitfunction[#] & /@ a;
        functionevalminimum = Min[Abs[functionevalarray]];
        minposition =
  Position[Abs[functionevalarray], functionevalminimum];
        lowpercentposition = minposition[[1]][[1]] *
    (pulsepeakposition - pulseminposition) / 150 + pulseminposition ;
(* Print[pulsecenterposition]; *)
(* Print[percentroots]; *)
Clear[dummyfitfunction];

(* find the % of max value position on pulse onset *)
      dummyfitfunction[y_] =
  (Fitfunction - pulsepeakvalue * uppercentage) /. x -> y;
        functionevalarray = dummyfitfunction[#] & /@ a;
        functionevalmaximum = Min[Abs[functionevalarray]];
        maxposition =
  Position[Abs[functionevalarray], functionevalmaximum];
        highpercentposition = maxposition[[1]][[1]] *
    (pulsepeakposition - pulseminposition) / 150 + pulseminposition ;

(* find the matching value on the other side
   of the heartbeat pulse for the %max and %min value*)
(*for the top descending value, take a short section
   of the falling side's data section *)
```

Single Point Delay - Time Functions

```
        datastart = IntegerPart[pulsepeakposition * acquisitionrate];
        dataend = IntegerPart[pulsepeakposition * acquisitionrate] + 500;
        datasection = Take[data, {crossingtable[[n]] - windowstart + datastart,
      crossingtable[[n]] - windowstart + dataend}];

offsetdatasection =
      Take[Abs[datasection - pulsepeakvalue * uppercentage], 100];
        descendingmaxposition =
      Position[offsetdatasection, Min[offsetdatasection]];
        descendingmaxtime = descendingmaxposition[[1]][[1]] / acquisitionrate +
      pulsepeakposition;
        offsetdatasection = Abs[datasection -
      IntegerPart[pulseminvalue * downpercentage]];
        descendingminposition = Position[offsetdatasection,
      Min[Abs[datasection - IntegerPart[pulseminvalue * downpercentage]]]];
        descendingmintime = descendingminposition[[1]][[1]] / acquisitionrate +
      pulsepeakposition;

(* rootsdummy =
        x/.FindRoot[ (Fitfunction-pulsepeakvalue*uppercentage)=0,
          {x, pulsepeakposition-.05, pulseminposition, pulsepeakposition}];
        If[functionwindowstart<rootsdummy<functionwindowend,
          percentroots=AppendTo[percentroots,rootsdummy]]
        Clear[rootsdummy]; *)
      {lowpercentposition, highpercentposition, descendingmintime,
        descendingmaxtime, pulseminposition, pulseminvalue}]
```

DescendingDelayFits performs linear fits between points on the pulse back side and determines the time delay between points on that linear slope. The points are determined on the pulse front side and then projected onto the backend slope of a given heartbeat pulse. 0% is the pulse onset, 100% is the pulse peak. uses FitPulseOnset and PulseOnsetTurningPoints to find turning point pairs for all pulse onsets identified in the crossingtable.

```
      DescendingDelayFits[data_, acquisitionrate_,
        crossingtable_, n_, windowstart_, windowend_,
        functionwindowstart_, functionwindowend_, onsetpercentage1_,
        onsetpercentage2_, onsetpercentage3_, onsetpercentage4_] :=
      Module[{Fitfunction, coeffs, chierror, pulsepeakposition,
        pulsepeakvalue, pulseminposition, pulseminvalue, pulsecentervalue,
        pulsecenterposition, a, dummyfitfunction, percentvalue1,
        percentvalue2, percentvalue3, percentvalue4, functionevalmaximum,
        minposition, maxposition, functionevalarray, percentposition1,
        percentposition2, percentposition3, percentposition4,
        zerocrossingposition, descendingposition, descendingminposition,
        datasection, datastart, dataend, offsetdatasection, descendingtime1,
        descendingtime2, descendingtime3, descendingtime4, descendingmintime,
        topdescendslopefit, topdescenderror, bottomdescendslopefit,
```

Single Point Delay - Time Functions

```
            bottomdescenderror, topfitdatasection, bottomfitsection},
        percentroots = {};
        datasection = {};
        offsetdatasection = {};
        a = {};
        b = {};
        functionevalarray = {};
        {Fitfunction, coeffs, chierror} =
               FitPulseOnset[data,
          acquisitionrate, crossingtable, n, windowstart, windowend];

(* find the max & min value positions of the pulse onset *)
        {pulseminposition, pulseminvalue, pulsepeakposition, pulsepeakvalue} =
         FunctionPeakFinderDiscrete[Fitfunction,
           functionwindowstart, functionwindowend, 100];

a = Range[pulseminposition, pulsepeakposition,
          (pulsepeakposition - pulseminposition) / 150] // N;

(* find the first % of max-
          min amplitude position on pulse onset, BY FITTING IT *)
                dummyfitfunction[y_] =
         (Fitfunction - ((pulsepeakvalue - pulseminvalue) * onsetpercentage1 +
               pulseminvalue)) /. x -> y;
                   functionevalarray = dummyfitfunction[#] & /@ a;
                   percentvalue1 = Min[Abs[functionevalarray]];
                   minposition = Position[Abs[functionevalarray], percentvalue1];
                   percentposition1 = minposition[[1]][[1]] *
            (pulsepeakposition - pulseminposition) / 150 + pulseminposition ;

(* find the second % of max-min amplitude position on pulse onset *)
                dummyfitfunction[y_] =
         (Fitfunction - ((pulsepeakvalue - pulseminvalue) * onsetpercentage2 +
               pulseminvalue)) /. x -> y;
                   functionevalarray = dummyfitfunction[#] & /@ a;
                   percentvalue2 = Min[Abs[functionevalarray]];
                   minposition = Position[Abs[functionevalarray], percentvalue2];
                   percentposition2 = minposition[[1]][[1]] *
            (pulsepeakposition - pulseminposition) / 150 + pulseminposition ;

(* find the third % of max-min amplitude position on pulse onset *)
                dummyfitfunction[y_] =
         (Fitfunction - ((pulsepeakvalue - pulseminvalue) * onsetpercentage3 +
               pulseminvalue)) /. x -> y;
                   functionevalarray = dummyfitfunction[#] & /@ a;
                   percentvalue3 = Min[Abs[functionevalarray]];
                   minposition = Position[Abs[functionevalarray], percentvalue3];
```

Single Point Delay - Time Functions

```
        percentposition3 = minposition[[1]][[1]] *
    (pulsepeakposition - pulseminposition) / 150 + pulseminposition;

(* find the fourth % of max-min amplitude position on pulse onset *)
        dummyfitfunction[y_] =
    (Fitfunction - ((pulsepeakvalue - pulseminvalue) * onsetpercentage4 +
        pulseminvalue)) /. x -> y;
        functionevalarray = dummyfitfunction[#] & /@ a;
        percentvalue4 = Min[Abs[functionevalarray]];
        minposition = Position[Abs[functionevalarray], percentvalue4];
        percentposition4 = minposition[[1]][[1]] *
    (pulsepeakposition - pulseminposition) / 150 + pulseminposition;
Clear[dummyfitfunction];

(* find the matching value on the other side of the heartbeat pulse,
 IN REAL DATA, for the % max and % min value *)
(* find the top descending values first (4 & 3),
 take a short section of the falling side's data section *)
(* get data of tailend of pulse, relative to the next pulse onset,
 unless it exceeds 550 points *)
    datastart = IntegerPart[pulsepeakposition * acquisitionrate];
    dataend = IntegerPart[pulsepeakposition * acquisitionrate] +
    (crossingtable[[n + 1]] - crossingtable[[n]] - 50);
If[
        dataend > 550,
        dataend = 550;
        ];

datasection = Take[data, {crossingtable[[n]] - windowstart + datastart,
    crossingtable[[n]] - windowstart + dataend}];

offsetdatasection =
Take[Abs[datasection - ((pulsepeakvalue - pulseminvalue) * onsetpercentage4 +
        pulseminvalue)], 100];
    descendingposition4 = Position[offsetdatasection,
 Min[offsetdatasection]];
    descendingtime4 = descendingposition4[[1]][[1]] / acquisitionrate +
 pulsepeakposition;

offsetdatasection =
Take[Abs[datasection - ((pulsepeakvalue - pulseminvalue) * onsetpercentage3 +
        pulseminvalue)], 100];
    descendingposition3 = Position[offsetdatasection,
 Min[offsetdatasection]];
    descendingtime3 = descendingposition3[[1]][[1]] / acquisitionrate +
 pulsepeakposition;
```

Single Point Delay - Time Functions

```
(* now for descending values of the lower half of the pulse (2 & 1) *)
    offsetdatasection = Abs[datasection -
    ((pulsepeakvalue - pulseminvalue) * onsetpercentage2 + pulseminvalue)];
    descendingposition2 = Position[offsetdatasection,
  Min[offsetdatasection]];
    descendingtime2 = descendingposition2[[1]][[1]] / acquisitionrate +
  pulsepeakposition;

offsetdatasection = Abs[datasection -
    ((pulsepeakvalue - pulseminvalue) * onsetpercentage1 + pulseminvalue)];
    descendingposition1 = Position[offsetdatasection,
  Min[offsetdatasection]];
    descendingtime1 = descendingposition1[[1]][[1]] / acquisitionrate +
  pulsepeakposition;

(* fit the data between top (4 & 3)
   and bottom (2 & 1) descending times linearly *)
    topfitdatasection = Take[datasection,
  {descendingposition4[[1]][[1]], descendingposition3[[1]][[1]]}];
    {topdescendslopefit, topdescenderror} = FitSection[topfitdatasection];

bottomfitdatasection = Take[datasection,
  {descendingposition2[[1]][[1]], descendingposition1[[1]][[1]]}];
    {bottomdescendslopefit, bottomdescenderror} =
  FitSection[bottomfitdatasection];

(* Now find the delay times on the fits *)
(* top section first *)
    b = Range[descendingposition4[[1]][[1]],
  descendingposition3[[1]][[1]], (descendingposition3[[1]][[1]] -
    descendingposition4[[1]][[1]]) / 60] // N;
    dummyfitfunction[y_] = (topdescendslopefit -
    ((pulsepeakvalue - pulseminvalue) * onsetpercentage4 +
    pulseminvalue)) /. x -> y;
    functionevalarray = dummyfitfunction[#] & /@ b;
    percentvalue4 = Min[Abs[functionevalarray]];
    minposition = Position[Abs[functionevalarray], percentvalue4];
    descendingfitposition4 =
  (minposition[[1]][[1]] + descendingposition4[[1]][[1]]) / acquisitionrate +
    pulsepeakposition // N;

dummyfitfunction[y_] =
  (topdescendslopefit - ((pulsepeakvalue - pulseminvalue) * onsetpercentage3 +
    pulseminvalue)) /. x -> y;
    functionevalarray = dummyfitfunction[#] & /@ b;
    percentvalue3 = Min[Abs[functionevalarray]];
    minposition = Position[Abs[functionevalarray], percentvalue3];
```

Single Point Delay - Time Functions

```
    descendingfitposition3 =
  (minposition [[1]][[1]] + descendingposition3[[1]][[1]]) / acquisitionrate +
    pulsepeakposition // N;

(* bottom section *)
  b = Range[descendingposition2[[1]][[1]],
      descendingposition1[[1]][[1]], (descendingposition1[[1]][[1]] -
          descendingposition2[[1]][[1]]) / 60] // N;
      dummyfitfunction[y_] = (topdescendslopefit -
      ((pulsepeakvalue - pulseminvalue) * onsetpercentage2 +
          pulseminvalue)) /. x -> y;
      functionevalarray = dummyfitfunction[#] & /@ b;
      percentvalue2 = Min[Abs[functionevalarray]];
      minposition = Position[Abs[functionevalarray], percentvalue2];
      descendingfitposition2 =
    (minposition [[1]][[1]] + descendingposition2[[1]][[1]]) / acquisitionrate +
      pulsepeakposition // N;

dummyfitfunction[y_] =
    (topdescendslopefit - ((pulsepeakvalue - pulseminvalue) * onsetpercentage1 +
          pulseminvalue)) /. x -> y;
      functionevalarray = dummyfitfunction[#] & /@ b;
      percentvalue1 = Min[Abs[functionevalarray]];
      minposition = Position[Abs[functionevalarray], percentvalue1];
      descendingfitposition1 =
    (minposition [[1]][[1]] + descendingposition1[[1]][[1]]) / acquisitionrate +
      pulsepeakposition // N;

(* rootsdummy    x/.
    FindRoot[ (Fitfunction-pulsepeakvalue*uppercentage)==0,
     {x, pulsepeakposition-.05, pulseminposition, pulsepeakposition}];
   If[functionwindowstart<rootsdummy<functionwindowend,
      percentroots=AppendTo[percentroots,rootsdummy]]
    Clear[rootsdummy]; *)
  {percentposition1, percentposition2, percentposition3,
    percentposition4, "xxx", descendingtime1, descendingfitposition1,
    descendingtime2, descendingfitposition2, descendingtime3,
    descendingfitposition3, descendingtime4, descendingfitposition4,
    "xxx", bottomdescendslopefit, bottomdescenderror, topdescendslopefit,
    topdescenderror, "xxx", pulsepeakvalue, pulseminvalue}]
```

FitSection accepts the data and returns a linear fit along with chisquared

Single Point Delay - Time Functions

```
FitSection[data_] :=
 Module[{FitFunction, ChiSquared,
    NormalizedDataSection, FunctionValue, datamax, datamin},
        lengthofNormSection = Dimensions@data;
        datamax = Max[data];
        datamin = Min[data];
        FitFunction = Fit[data, {1, x}, x];
    For[ChiSquared = 0;
        i = 1, i < lengthofNormSection[[1]] - 1, i++,
            FunctionValue = FitFunction /. x -> i ;
            ChiSquared =
    ChiSquared + (FunctionValue - data[[i]])^2 / (datamax - datamin)^2;
        ];
    {FitFunction, ChiSquared}]
```

KillPoorChisquared wipes out points in the crossingtable with chisquared exceeding certain value. Be careful to give the correct crossing range.

```
KillPoorChisquared[crossingtable_, nstart_,
  nend_, chisquaredtable_, chisquaredthreshold_] :=
 Module[{izero, i, modifiedcrossingtable, killchilist,
    listlength, modifiedchisquaredlist},
    For[listlength = nend - nstart;
        killchilist = {};
        modifiedcrossingtable = {};
        i = 1, i < listlength, i++,
            If[
                chisquaredtable[[i]] > chisquaredthreshold,
                    killchilist = AppendTo[killchilist, {i}];
            ];
            If[
                chisquaredtable[[i]] == 0,
                    killchilist = AppendTo[killchilist, {i}];
            ];
        ];
        killchilist = Reverse@killchilist;
        modifiedchisquaredlist = Delete[chisquaredtable, killchilist];
        modifiedcrossingtable = Delete[crossingtable, killchilist];
        {modifiedchisquaredlist, modifiedcrossingtable}]
```

Moens Korteweg equation, speed in cm/s. $E = .94 \cdot 10^6$ dyne/cm2 is a quote for the brachial Young's modulus

Single Point Delay - Time Functions

Y = 0.94 *10^6; (*dyne/cm^2*)
h = 0.08; (* cm , arterial wall thickness *)
R = 0.18; (* cm, brachial artery radius *)
ρ = 1.16;

$$\sqrt{\frac{h\,Y\,e^{\xi p}}{2\rho R}}$$

$$\Delta c[\xi\_,\ p\_] := \frac{\sqrt{\frac{h\,Y\,e^{\xi p}}{2\rho R}}}{1}$$

$$424.354\sqrt{e^{p\xi}}$$

$$\text{pressure}[\xi\_,\ t\_,\ \text{offset}\_] := (-2/\xi)\,\text{Log}\left[\left(t\sqrt{\frac{h\,Y}{2\rho R}}\right)\Big/100\right] + \text{offset};$$

OnsetDelay calculates a sequence of eight delay times on the pulse front end which are then used to calculate the effective delay time, with each delay calculated here given individual weight factors.

```
OnsetDelays[data_, acquisitionrate_, crossingtable_,
    n_, windowstart_, windowend_, functionwindowstart_,
    functionwindowend_, onsetpercentage1_, onsetpercentage2_,
    onsetpercentage3_, onsetpercentage4_, onsetpercentage5_,
    onsetpercentage6_, onsetpercentage7_, onsetpercentage8_] :=
  Module[{Fitfunction, coeffs, chierror, pulsepeakposition, pulsepeakvalue,
      pulseminposition, pulseminvalue, pulsecentervalue, pulsecenterposition,
      a, dummyfitfunction, percentvalue1, percentvalue2, percentvalue3,
      percentvalue4, percentvalue5, percentvalue6, percentvalue7,
      percentvalue8, functionevalmaximum, minposition, maxposition,
      functionevalarray, percentposition1, percentposition2, percentposition3,
      percentposition4, percentposition5, percentposition6, percentposition7,
      percentposition8, zerocrossingposition, datasection, datastart, dataend},
    percentroots = {};
    datasection = {};
    offsetdatasection = {};
    a = {};
    b = {};
    functionevalarray = {};
    {Fitfunction, coeffs, chierror} =
        FitPulseOnset[data,
      acquisitionrate, crossingtable, n, windowstart, windowend];

(* find the max & min value positions of the pulse onset *)
    {pulseminposition, pulseminvalue, pulsepeakposition, pulsepeakvalue} =
      FunctionPeakFinderDiscrete[Fitfunction,
        functionwindowstart, functionwindowend, 100];

a = Range[pulseminposition, pulsepeakposition,
```

Single Point Delay - Time Functions

```
        (pulsepeakposition - pulseminposition) / 150] // N;

(* find the first % of max-
   min amplitude position on pulse onset, BY FITTING IT *)
        dummyfitfunction[y_] =
 (Fitfunction - ((pulsepeakvalue - pulseminvalue) * onsetpercentage1 +
     pulseminvalue)) /. x -> y;
        functionevalarray = dummyfitfunction[#] & /@ a;
        percentvalue1 = Min[Abs[functionevalarray]];
        minposition = Position[Abs[functionevalarray], percentvalue1];
        percentposition1 = minposition[[1]][[1]] *
   (pulsepeakposition - pulseminposition) / 150 + pulseminposition ;

(* find the second % of max-min amplitude position on pulse onset *)
        dummyfitfunction[y_] =
 (Fitfunction - ((pulsepeakvalue - pulseminvalue) * onsetpercentage2 +
     pulseminvalue)) /. x -> y;
        functionevalarray = dummyfitfunction[#] & /@ a;
        percentvalue2 = Min[Abs[functionevalarray]];
        minposition = Position[Abs[functionevalarray], percentvalue2];
        percentposition2 = minposition[[1]][[1]] *
   (pulsepeakposition - pulseminposition) / 150 + pulseminposition ;

(* find the third % of max-min amplitude position on pulse onset *)
        dummyfitfunction[y_] =
 (Fitfunction - ((pulsepeakvalue - pulseminvalue) * onsetpercentage3 +
     pulseminvalue)) /. x -> y;
        functionevalarray = dummyfitfunction[#] & /@ a;
        percentvalue3 = Min[Abs[functionevalarray]];
        minposition = Position[Abs[functionevalarray], percentvalue3];
        percentposition3 = minposition[[1]][[1]] *
   (pulsepeakposition - pulseminposition) / 150 + pulseminposition ;

(* find the fourth % of max-min amplitude position on pulse onset *)
        dummyfitfunction[y_] =
 (Fitfunction - ((pulsepeakvalue - pulseminvalue) * onsetpercentage4 +
     pulseminvalue)) /. x -> y;
        functionevalarray = dummyfitfunction[#] & /@ a;
        percentvalue4 = Min[Abs[functionevalarray]];
        minposition = Position[Abs[functionevalarray], percentvalue4];
        percentposition4 = minposition[[1]][[1]] *
   (pulsepeakposition - pulseminposition) / 150 + pulseminposition ;

(* find the fifth % of max-
   min amplitude position on pulse onset, BY FITTING IT *)
        dummyfitfunction[y_] =
 (Fitfunction - ((pulsepeakvalue - pulseminvalue) * onsetpercentage5 +
```

Single Point Delay - Time Functions

```
        pulseminvalue)) /. x → y;
    functionevalarray = dummyfitfunction[#] & /@ a;
    percentvalue5 = Min[Abs[functionevalarray]];
    minposition = Position[Abs[functionevalarray], percentvalue5];
    percentposition5 = minposition[[1]][[1]] *
(pulsepeakposition - pulseminposition) / 150 + pulseminposition;

(* find the sixth % of max-min amplitude position on pulse onset *)
        dummyfitfunction[y_] =
 (Fitfunction - ((pulsepeakvalue - pulseminvalue) * onsetpercentage6 +
    pulseminvalue)) /. x → y;
    functionevalarray = dummyfitfunction[#] & /@ a;
    percentvalue6 = Min[Abs[functionevalarray]];
    minposition = Position[Abs[functionevalarray], percentvalue6];
    percentposition6 = minposition[[1]][[1]] *
(pulsepeakposition - pulseminposition) / 150 + pulseminposition;

(* find the seventh % of max-min amplitude position on pulse onset *)
        dummyfitfunction[y_] =
 (Fitfunction - ((pulsepeakvalue - pulseminvalue) * onsetpercentage7 +
    pulseminvalue)) /. x → y;
    functionevalarray = dummyfitfunction[#] & /@ a;
    percentvalue7 = Min[Abs[functionevalarray]];
    minposition = Position[Abs[functionevalarray], percentvalue7];
    percentposition7 = minposition[[1]][[1]] *
(pulsepeakposition - pulseminposition) / 150 + pulseminposition;

(* find the eigth % of max-min amplitude position on pulse onset *)
        dummyfitfunction[y_] =
 (Fitfunction - ((pulsepeakvalue - pulseminvalue) * onsetpercentage8 +
    pulseminvalue)) /. x → y;
    functionevalarray = dummyfitfunction[#] & /@ a;
    percentvalue8 = Min[Abs[functionevalarray]];
    minposition = Position[Abs[functionevalarray], percentvalue8];
    percentposition8 = minposition[[1]][[1]] *
(pulsepeakposition - pulseminposition) / 150 + pulseminposition;
Clear[dummyfitfunction];

{percentposition1, percentposition2, percentposition3, percentposition4,
 "xxx", percentposition5, percentposition6, percentposition7,
 percentposition8, "xxx", pulsepeakvalue, pulseminvalue}]
```

What is claimed is:

1. A method of monitoring blood pressure, which comprises: determining delay time between predetermined points on a heartbeat pulse, and using the delay time to obtain a measurement of blood pressure, wherein the predetermined points on the heartbeat pulse are on an onset slope of the pulse, and wherein plural delay times are measured between predetermined points on the onset slope that are located on a portion of the onset slope that extends between the peak of the pulse and 50% of the peak of the pulse.

2. A method according to claim 1, wherein the plural delay times are averaged.

3. Apparatus for monitoring blood pressure, comprising: a sensor that detects a heartbeat pulse at a site on a body through which blood flows, and a unit that determines delay time between predetermined points on the front side or between predetermined points on the back side of the detected heartbeat pulse and that uses the delay time to obtain a measurement of blood pressure, wherein the unit measures plural delay times between the predetermined points on the heartbeat pulse.

4. Apparatus according to claim 3, wherein the plural delay times are averaged.

5. A method of monitoring blood pressure, which comprises: determining plural delay times between predetermined points on the front side or between predetermined points on the back side of a heartbeat pulse, and using the plural delay times to obtain a measurement of blood pressure.

6. A method according to claim 5, wherein the plural delay times are averaged.

7. A process of determining changes in blood pressure, which comprises: repeating the method of claim 5 for each of a series of heartbeat pulses over a period of time; and producing an output of blood pressure measurement over the period of time.

8. A process of determining changes in blood pressure, which comprises: repeating the method of claim 6 for each of a series of heartbeat pulses over a period of time; and producing an output of blood pressure measurement over the period of time.

9. A process according to claim 7, wherein variations of the blood pressure output are used to determined Pulsus Paradoxus.

10. A process according to claim 9, wherein the output is filtered to isolate Pulsus Paradoxus modulations.

* * * * *

UNITED STATES PATENT AND TRADEMARK OFFICE
CERTIFICATE OF CORRECTION

| | | |
|---|---|---|
| PATENT NO. | : 7,087,025 B2 | Page 1 of 1 |
| APPLICATION NO. | : 10/502932 | |
| DATED | : August 8, 2006 | |
| INVENTOR(S) | : Martin C. Baruch | |

It is certified that error appears in the above-identified patent and that said Letters Patent is hereby corrected as shown below:

In the Specification, Col. 1, lines 13-14, Please add,

This invention was made with Government support under Contract Number N00014-04-C-02040004 awarded by the Department of the Navy. The Government has certain rights in the invention.

Signed and Sealed this
Second Day of July, 2013

Teresa Stanek Rea
*Acting Director of the United States Patent and Trademark Office*